(12) United States Patent
Rajaraman et al.

(10) Patent No.: US 11,351,537 B2
(45) Date of Patent: Jun. 7, 2022

(54) SYSTEM AND METHOD FOR FORMING A BIOLOGICAL MICRODEVICE

(71) Applicant: University of Central Florida Research Foundation, Inc., Orlando, FL (US)

(72) Inventors: Swaminathan Rajaraman, Winter Park, FL (US); Avra Kundu, Orlando, FL (US); Tariq Ausaf, Sebring, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 906 days.

(21) Appl. No.: 15/887,556

(22) Filed: Feb. 2, 2018

(65) Prior Publication Data

US 2019/0240658 A1 Aug. 8, 2019

(51) Int. Cl.
*B81C 1/00* (2006.01)
*B81B 1/00* (2006.01)
(Continued)

(52) U.S. Cl.
CPC ... *B01L 3/502707* (2013.01); *A61M 37/0015* (2013.01); *B33Y 10/00* (2014.12); *B81B 1/00* (2013.01); *B81B 1/006* (2013.01); *B81C 1/00095* (2013.01); *B81C 1/00111* (2013.01); *G01N 33/4836* (2013.01); *G03F 7/0037* (2013.01); *A61M 2037/0046* (2013.01); *A61M 2037/0053* (2013.01);
(Continued)

(58) Field of Classification Search
CPC .................................................. B81C 1/00111
See application file for complete search history.

(56) References Cited

U.S. PATENT DOCUMENTS

| | | | |
|---|---|---|---|
| 2012/0157804 A1* | 6/2012 | Rogers | A61B 5/076 600/345 |
| 2017/0231518 A1* | 8/2017 | Dayeh | B81B 1/00 600/544 |

(Continued)

OTHER PUBLICATIONS

ADAFRUIT https://www.adafruit.com/product/166.

(Continued)

*Primary Examiner* — Moazzam Hossain
(74) *Attorney, Agent, or Firm* — Timothy H. Van Dyke; Wolter, Van Dyke, Davis, PLLC

(57) ABSTRACT

A method for forming a biological microdevice includes applying a biocompatible coarse scale additive process with an additive device and a biocompatible material to form an object. The coarse scale is a dimension not less than about 100 μm. The method also includes applying a biocompatible fine scale subtractive process with a subtractive device to the object. The fine scale is a dimension not greater than about 1000 μm. The method also includes moving the object between the additive device and the subtractive device. A system is also provided for performing the above method and includes the additive device, the subtractive device, a means for transporting the object between the additive device and subtractive device and a processor with a memory including instructions to perform one or more of the above method steps.

18 Claims, 22 Drawing Sheets

(51) Int. Cl.

| | |
|---|---|
| *G01N 33/483* | (2006.01) |
| *B01L 3/00* | (2006.01) |
| *A61M 37/00* | (2006.01) |
| *G03F 7/00* | (2006.01) |
| *B33Y 10/00* | (2015.01) |
| *G03F 7/16* | (2006.01) |
| *G03F 7/20* | (2006.01) |

(52) U.S. Cl.
CPC ............ *B81B 2203/0338* (2013.01); *B81B 2203/0361* (2013.01); *B81B 2203/04* (2013.01); *B81C 2201/019* (2013.01); *B81C 2201/0146* (2013.01); *B81C 2201/0159* (2013.01); *B81C 2201/0185* (2013.01); *G03F 7/162* (2013.01); *G03F 7/168* (2013.01); *G03F 7/2004* (2013.01)

(56) References Cited

U.S. PATENT DOCUMENTS

2018/0353750 A1* 12/2018 Hetke .................... A61B 5/287
2019/0021619 A1* 1/2019 Dayeh .................... B81B 1/008

OTHER PUBLICATIONS

ALL3DP https://all3dp.com/1/best-resin-dlp-sla-3d-printer-kit-stereolithography/.
Aoyagi, S., Izumi, H., Isono, Y., Fukuda, M. & Ogawa, H. Laser fabrication of high aspect ratio thin holes on biodegradable polymer and its application to a microneedle. Sensors and Actuators A: Physical 139, 293-302 (2007).
Axion Biosystems https://www.axionbiosystems.com/.
Chen, W., Li, H., Shi, D., Liu, Z. & Yuan, W. Microneedles as a delivery system for gene therapy. Frontiers in pharmacology 7 (2016).
Choi, S.-O et al. An electrically active microneedle array for electroporation. Biomedical microdevices 12, 263-273 (2010).
Chu, L. Y., Choi, S. O. & Prausnitz, M. R. Fabrication of dissolving polymer microneedles for controlled drug encapsulation and delivery: bubble and pedestal microneedle designs. Journal of pharmaceutical sciences 99, 4228-4238 (2010).
Donnelly, R. F. et al. Design, optimization and characterisation of polymeric microneedle arrays prepared by a novel laser-based micromoulding technique. Pharmaceutical research 28, 41-57 (2011).
Donnelly, R. F. et al. Hydrogel-forming microneedles prepared from "super swelling" polymers combined with lyophilised wafers for transdermal drug delivery. PLoS One 9, e111547 (2014).
Donnelly, R. F., Singh, T. R. R. & Woolfson, A. D. Microneedle-based drug delivery systems: microfabrication, drug delivery, and safety. Drug delivery 17, 187-207 (2010). from Clean Rooms to Makerspaces. Trends in Biotechnology (2017).
Form Labs https://www.support.formlabs.eom/hc/en-us/articles/115000024604-post-curingprints.
Gallagher, A., Ni Annaidh, A. & Bruyère, K. in IRCOBI Conference 2012, Sep. 12-14, 2012, Dublin (Ireland). (International Research Council on the Biomechanics of Injury).
Ghane-Motlagh, B. & Sawan, M. in Advances in Biomedical Engineering (ICABME), 2013 2nd International Conference on. 38-41 (IEEE).
Glick, C. C. et al. Rapid assembly of multilayer microfluidic structures via 3Dprinted transfer molding and bonding. Microsystems & Nanoengineering 2, 16063 (2016).
Han, M. et al. A novel fabrication process for out-of-plane microneedle sheets of biocompatible polymer. Journal of Micromechanics and Microengineering 17, 1184 (2007).
Huang, H. & Fu, C. Different fabrication methods of out-of-plane polymer hollow needle arrays and their variations. Journal of Micromechanics and Microengineering 17, 393 (2007).
Indermun, S. et al. Current advances in the fabrication of microneedles for transdermal delivery. Journal of controlled release 185, 130-138 (2014).
Ita, K. Transdermal delivery of drugs with microneedles—Potential and challenges. Pharmaceutics 7, 90-105 (2015).
Ito, Y., Hagiwara, E., Saeki, A., Sugioka, N. & Takada, K. Feasibility of microneedles for percutaneous absorption of insulin. European journal of pharmaceutical sciences 29, 82-88 (2006).
Karnati, G., Aguilar, R., Arrowood, C., Ross, J. & Rajaraman, S. Rajaraman. Micromachining on and of Transparent Polymers for Patterning Electrodes and Growing Electrically Active Cells for Biosensor Applications. Micromachines 8, 250 (2017).
Kim, J.-H., Kang, G., Nam, Y. & Choi, Y.-K. Surface-modified microelectrode array with flake nanostructure for neural recording and stimulation. Nanotechnology 21, 085303 (2010).
Kim, R., Joo, S., Jung, H., Hong, N. & Nam, Y. Recent trends in microelectrode array technology for in vitro neural interface platform. Biomedical Engineering Letters 4, 129-141 (2014).
Kim, Y.-C., Quan, F.-S., Compans, R. W., Kang, S.-M. & Prausnitz, M. R. Formulation of microneedles coated with influenza virus-like particle vaccine. Aaps Pharmscitech 11, 1193-1201 (2010).
Konar, D., Devarasetty, M., Yildiz, D. V., Atala, A. & Murphy, S. V. Lung-On-A-Chip Technologies for Disease Modeling and Drug Development. Biomedical engineering and computational biology 7, 17 (2016).
Larraneta, E., Lutton, R. E., Woolfson, A. D. & Donnelly, R. F. Microneedle arrays as transdermal and intradermal drug delivery systems: Materials science, manufacture and commercial development. Materials Science and Engineering: R: Reports 104, 1-32 (2016).
Lippmann, J. M., Geiger, E. J. & Pisano, A. P. Polymer investment molding: method for fabricating hollow, microscale parts. Sensors and Actuators A: Physical 134, 2-10 (2007).
McAllister, D. V. et al. Microfabricated needles for transdermal delivery of macromolecules and nanoparticles: fabrication methods and transport studies. Proceedings of the National Academy of Sciences 100, 13755-13760 (2003).
Multichannel Systems http://www.multichannelsystems.com/.
Nam, K.-H., Smith, A. S., Lone, S., Kwon, S. & Kim, D.-H. Biomimetic 3D, "J. Lab. Autom." pp. 201-215, vol. 20, issue 3 (2015).
O'Mahony, C. Structural characterization and in-vivo reliability evaluation of silicon microneedles. Biomedical microdevices 16, 333-343 (2014).
Park, J.-H., Allen, M. G. & Prausnitz, M. R. Polymer microneedles for controlledrelease drug delivery. Pharmaceutical research 23, 1008-1019 (2006).
Rajaraman, S. in 231st ECS Meeting (May 28-Jun. 1, 2017). (Ecs).
Rezaei Kolahchi, A. et al. Microfluidic-Based Multi-Organ Platforms for Drug Discovery. Micromachines 7, 162 (2016).
Ripolin, A. et al. Successful application of large microneedle patches by human volunteers. International journal of pharmaceutics 521, 92-101 (2017).
Woodard, C. M., B. A. Campos, S. H. Kuo, M. J. Nirenberg, M. W. Nestor, M. Zimmer, E. V. Mosharov, D. Sulzer, H. Y. Zhou, D. Paull, L. Clark, E. E. Schadt, S. P. Sardi, L. Rubin, K. Eggan, M. Brock, S. Lipnick, M. Rao, S. Chang, A. Q. Li and S. A. Noggle. "Ipsc-Derived Dopamine Neurons Reveal Differences between Monozygotic Twins Discordant for Parkinson's Disease." Cell Reports 9, No. 4 (2014): 1173-1182.
Shipulya, N.D., Konakov, S.A. & Krzhizhanovskaya, V.V. Development and simulation of microfluidic Wheatstone bridge for high-precision sensor. Journal of Physics: Conference Series, 738, 1 (2016).
3Spira, M. E. & Hai, A. Multi-electrode array technologies for neuroscience and cardiology. Nature nanotechnology 8, 83-94 (2013).
Sullivan, S. P., Murthy, N. & Prausnitz, M. R. Minimally invasive protein delivery with rapidly dissolving polymer microneedles. Advanced materials 20, 933-938 (2008).
Temiz, Y., Lovchik, R. D., Kaigala, G. V. & Delamarche, E. Lab-on-a-chip devices: How to close and plug the lab? Microelec-

(56) References Cited

OTHER PUBLICATIONS tronic Engineering 132, 156-175 (2015). tissue models for advanced high-throughput drug screening. Journal of laboratory automation 20, 201-215 (2015).

Wainger, B. J., E. Kiskinis, C. Mellin, O. Wiskow, S. S. W. Han, J. Sandoe, N. P. Perez, L. A. Williams, S. Lee, G. Boulting, J. D. Berry, R. H. Brown, M. E. Cudkowicz, B. P. Bean, K. Eggan and C. J. Woolf. "Intrinsic Membrane Hyperexcitability of Amyotrophic Lateral Sclerosis Patient-Derived Motor Neurons." Cell Reports 7, No. 1 (2014): 1-11.

Walsh, D. I., Kong, D. S., Murthy, S. K. & Carr, P. A. Enabling Microfluidics, "Trends in Biotech.", pp. 383-392, vol. 35, Issue 5 (2017).

Wang, P. M., Cornwell, M., Hill, J. & Prausnitz, M. R. Precise microinjection into skin using hollow microneedles. Journal of investigative dermatology 126, 1080-1087 (2006).

Ausaf, T., et al., 3D Printing Ink Casting and Lamination, "Nanoscience Tech. Center" pp. 1-2 (2017).

Carrington, S., MicroTAS Late News Posters, "Lab on a Chip Block", pp. 1-3 (2017).

\* cited by examiner

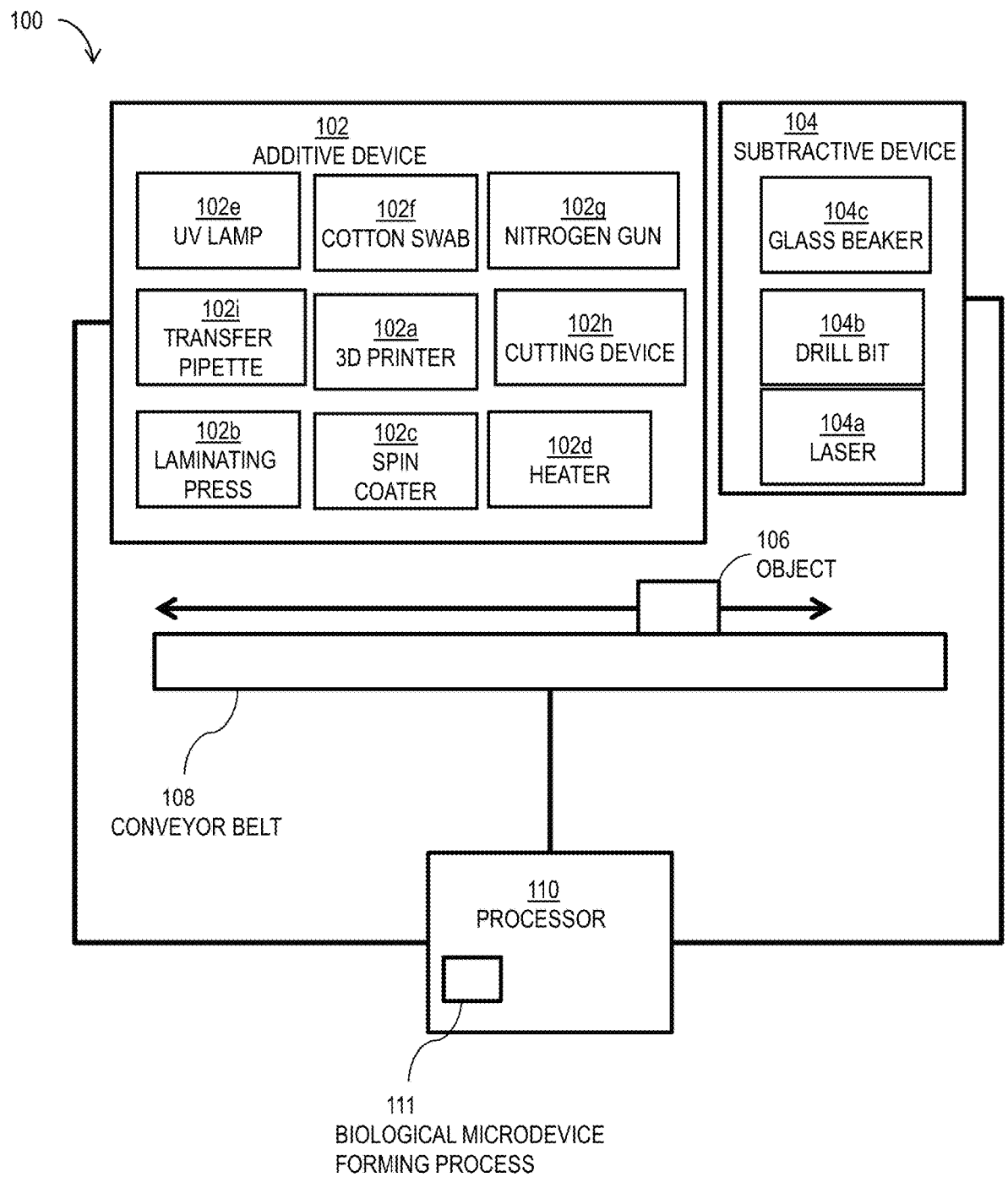

FIG. 3C
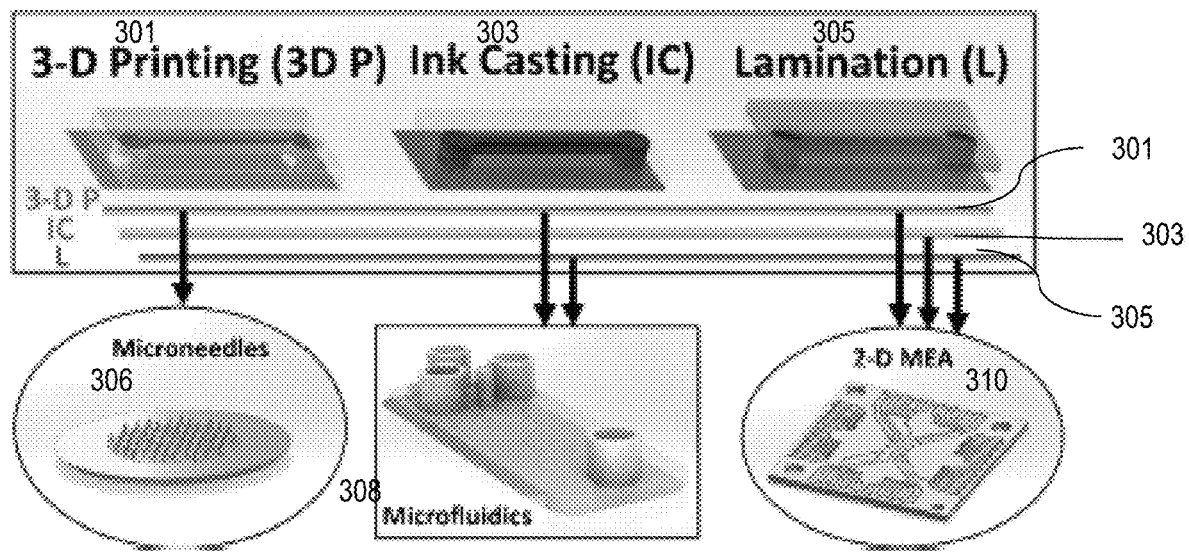
FIG. 3D
306
MICRONEEDLE
ARRAY
FIG. 3E
308
MF CHANNEL
FIG. 3F
310
MEA
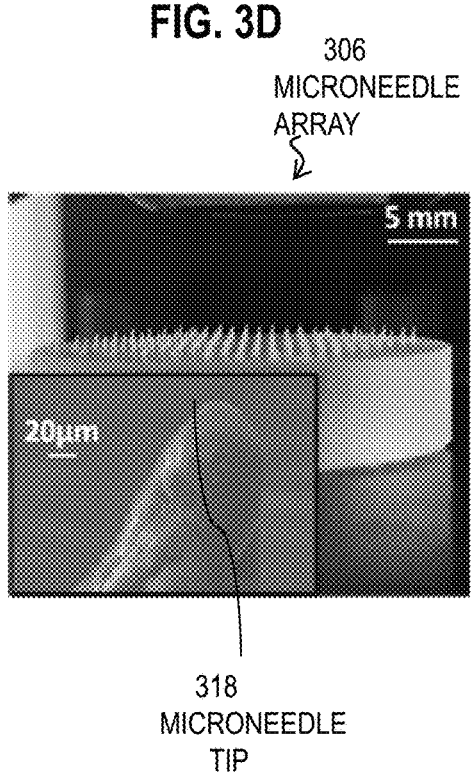
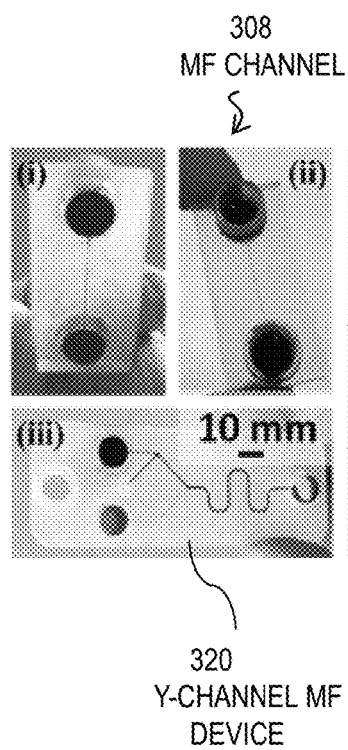
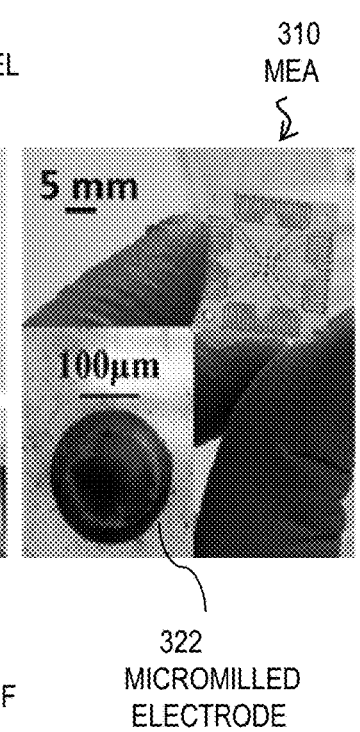
318
MICRONEEDLE
TIP
320
Y-CHANNEL MF
DEVICE
322
MICROMILLED
ELECTRODE

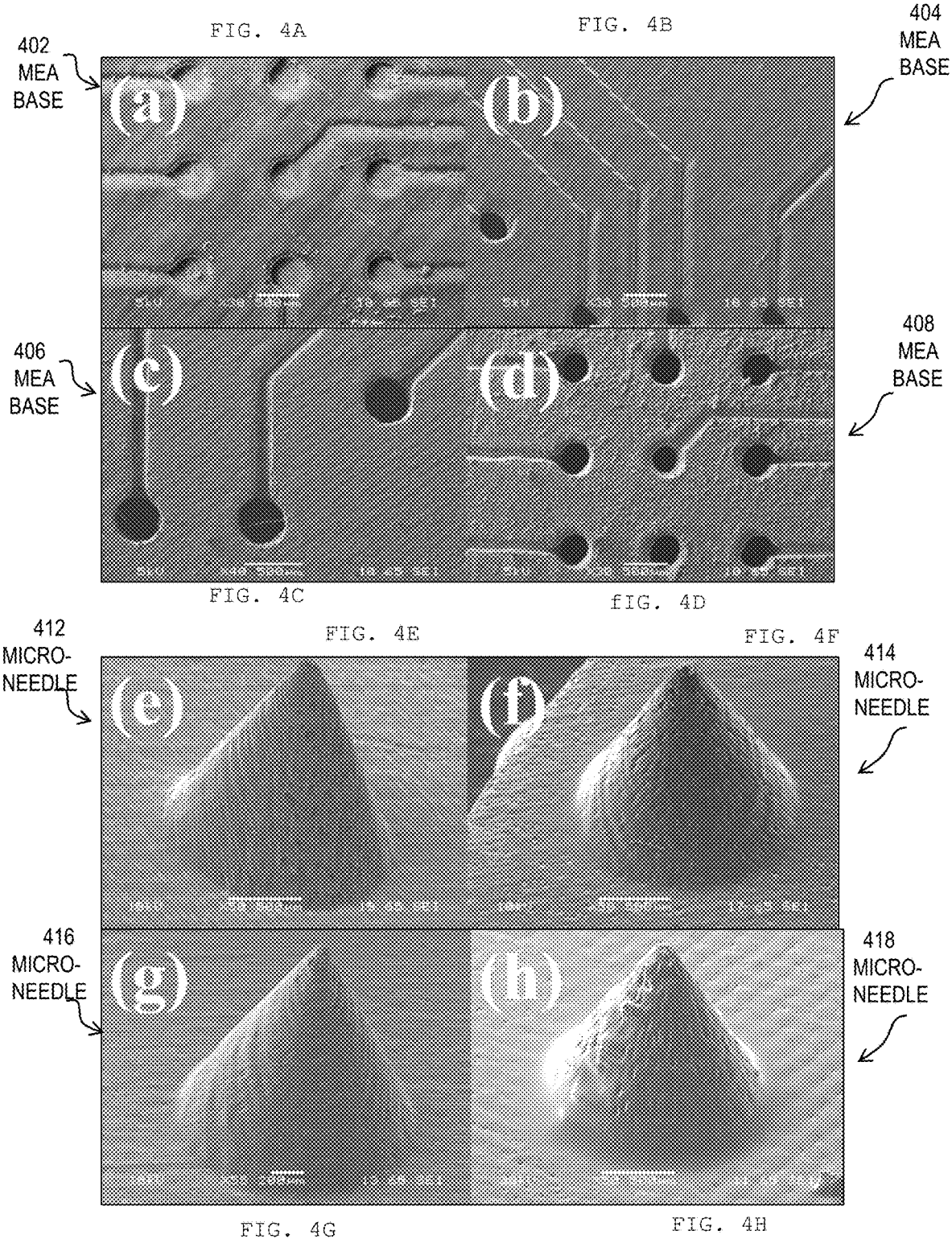

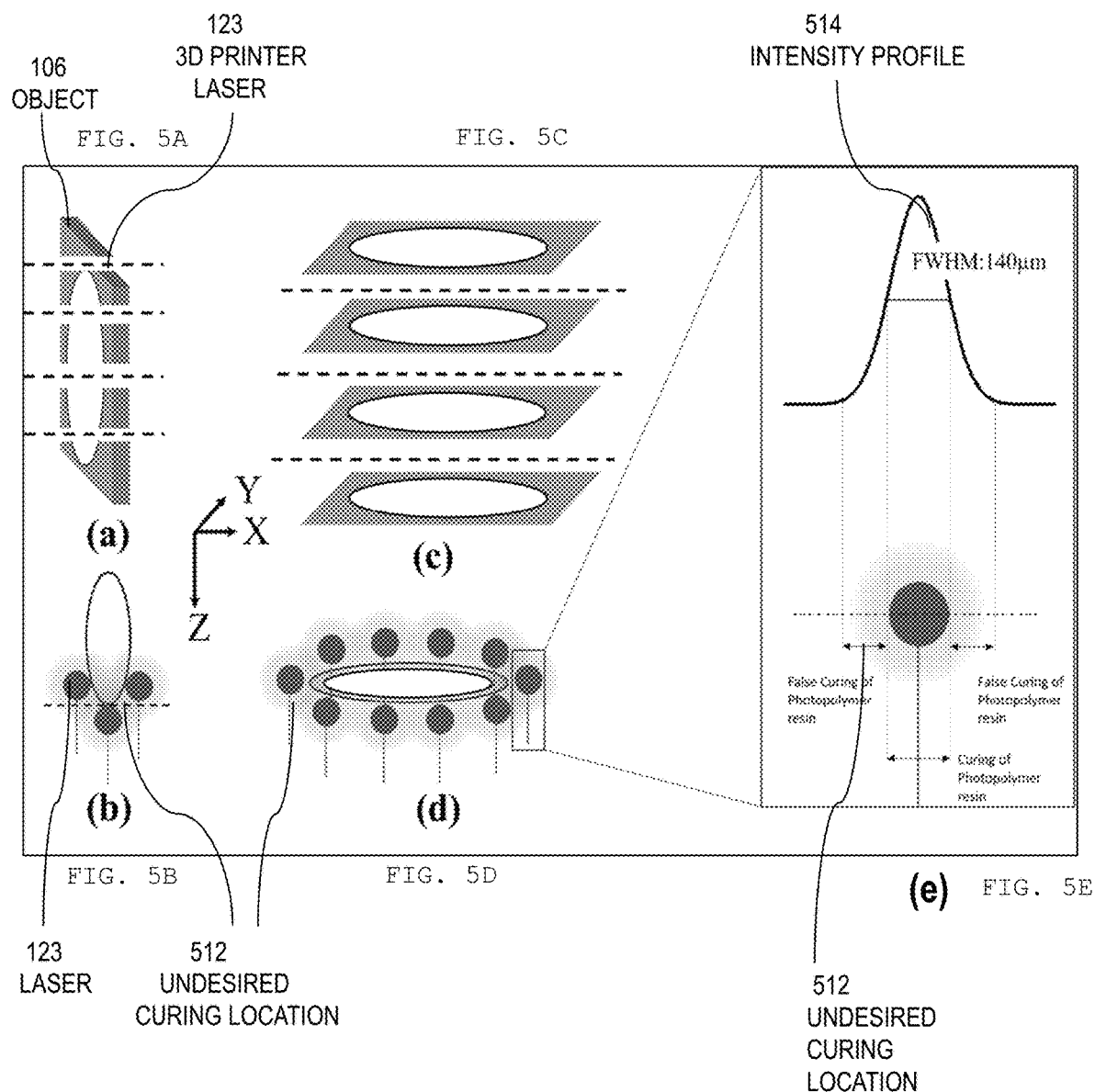

602 NONLAMINATED MICROELECTRODE
604 LAMINATED MICRODRILLED ELECTRODE
606 LAMINATED LASER MICROMACHINED ELECTRODE
608 CROSSLINKED LASER MICROMACHINED ELECTRODE

310 PACKAGED MEA

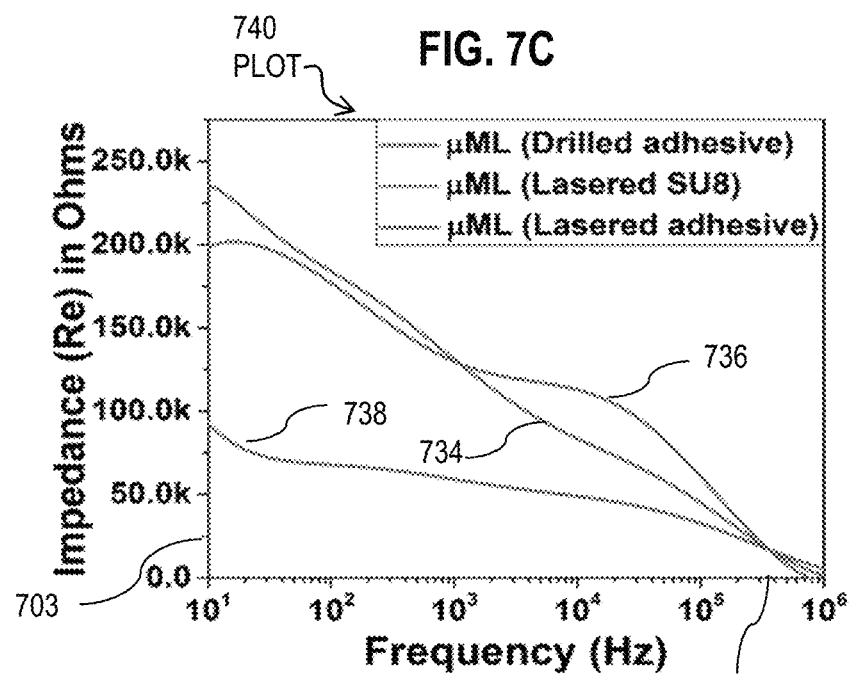
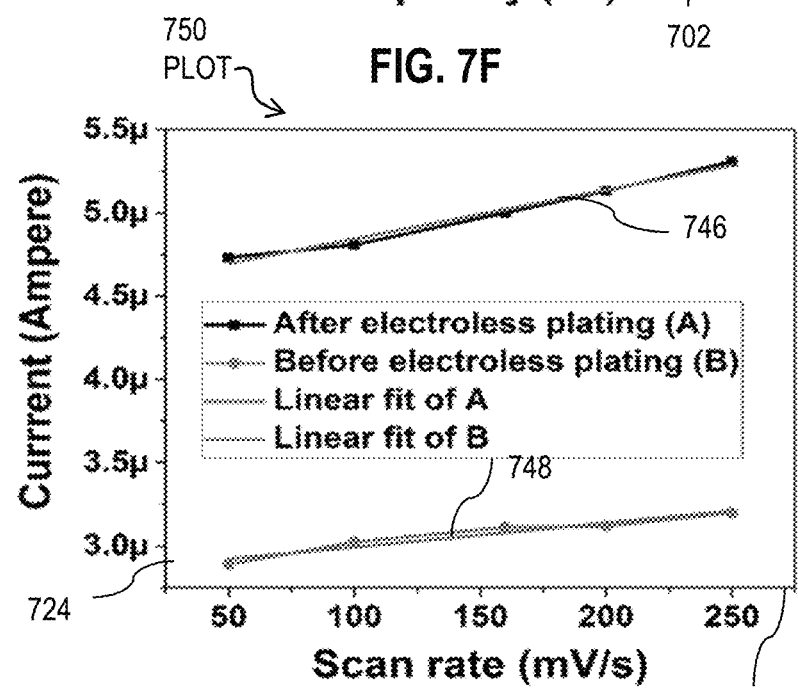

802 MEA
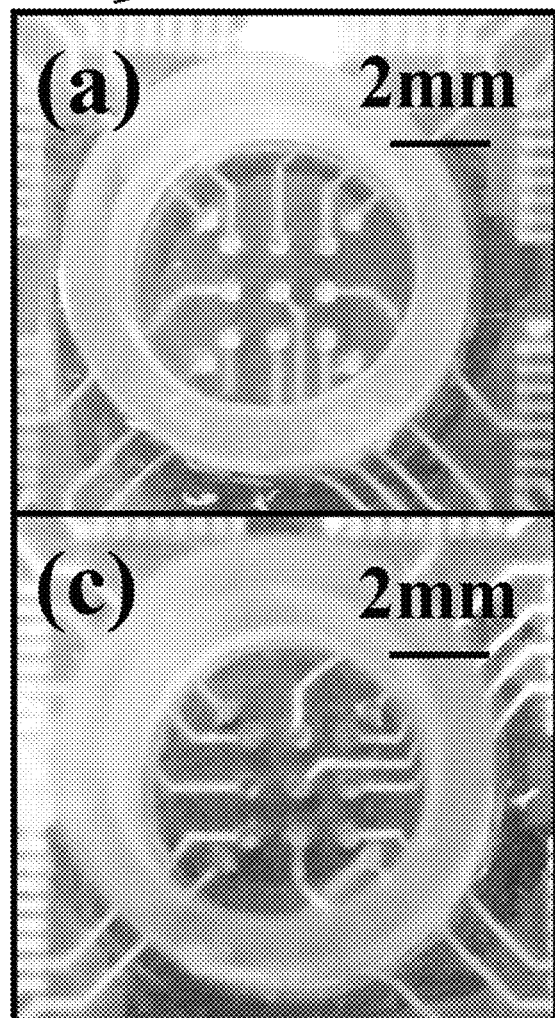
FIG. 8A
804 MEA
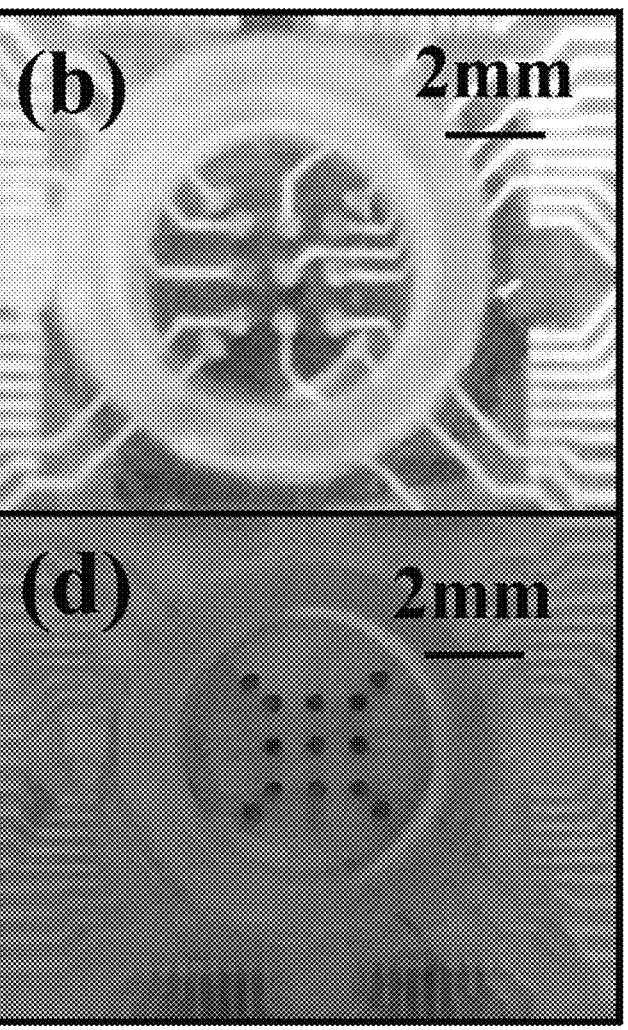
FIG. 8B
806 MEA
FIG. 8C
808 MEA
FIG. 8D

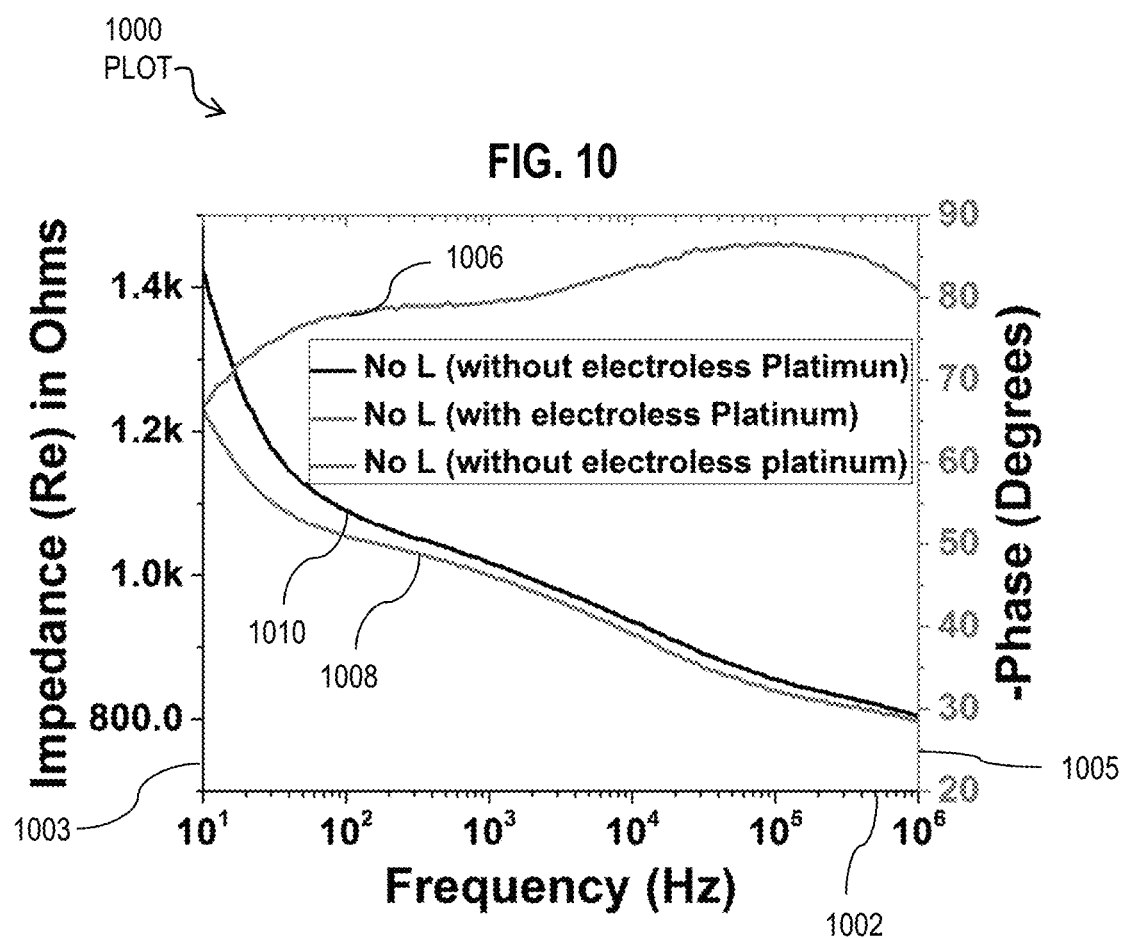

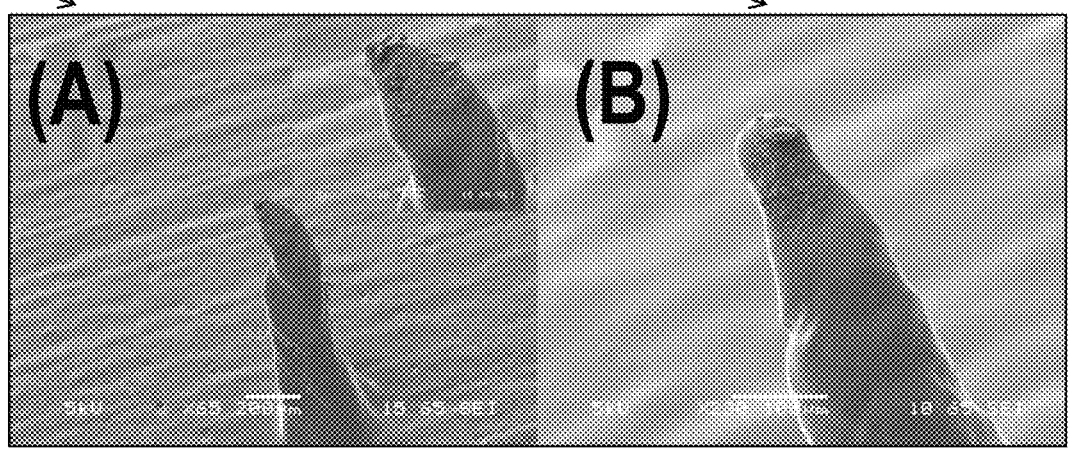
FIG. 11A    FIG. 11B
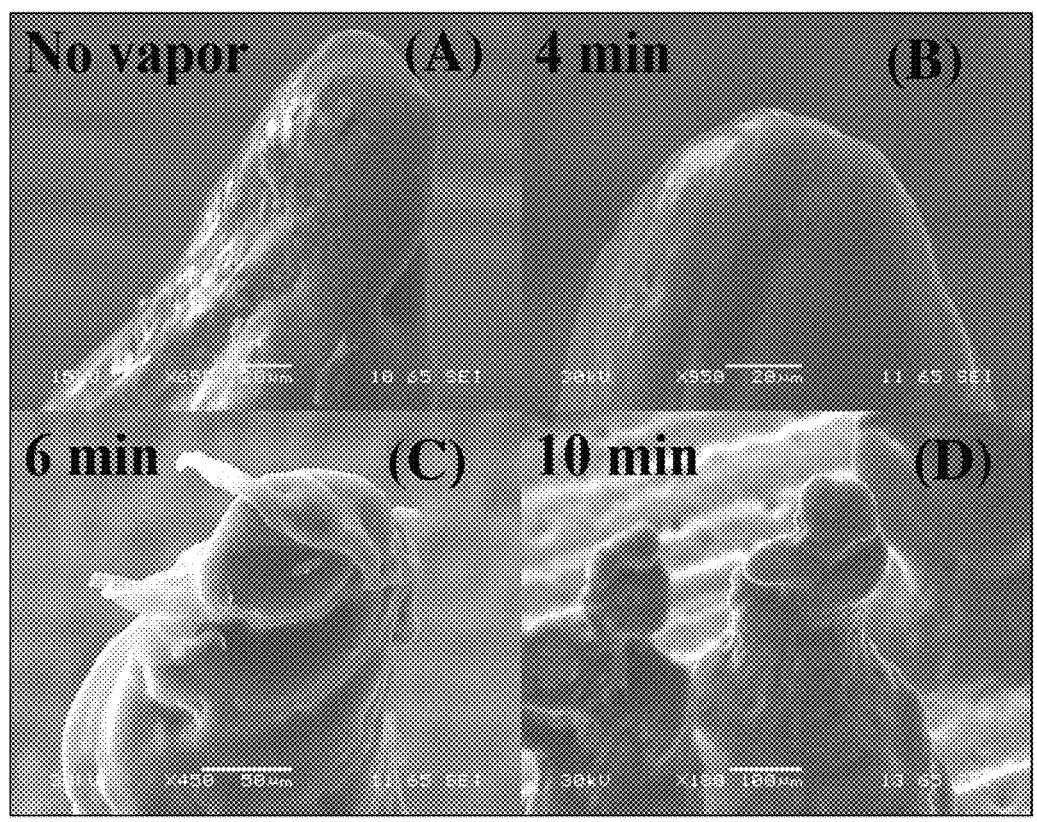
FIG. 12A    FIG. 12B
FIG. 12C    FIG. 12D

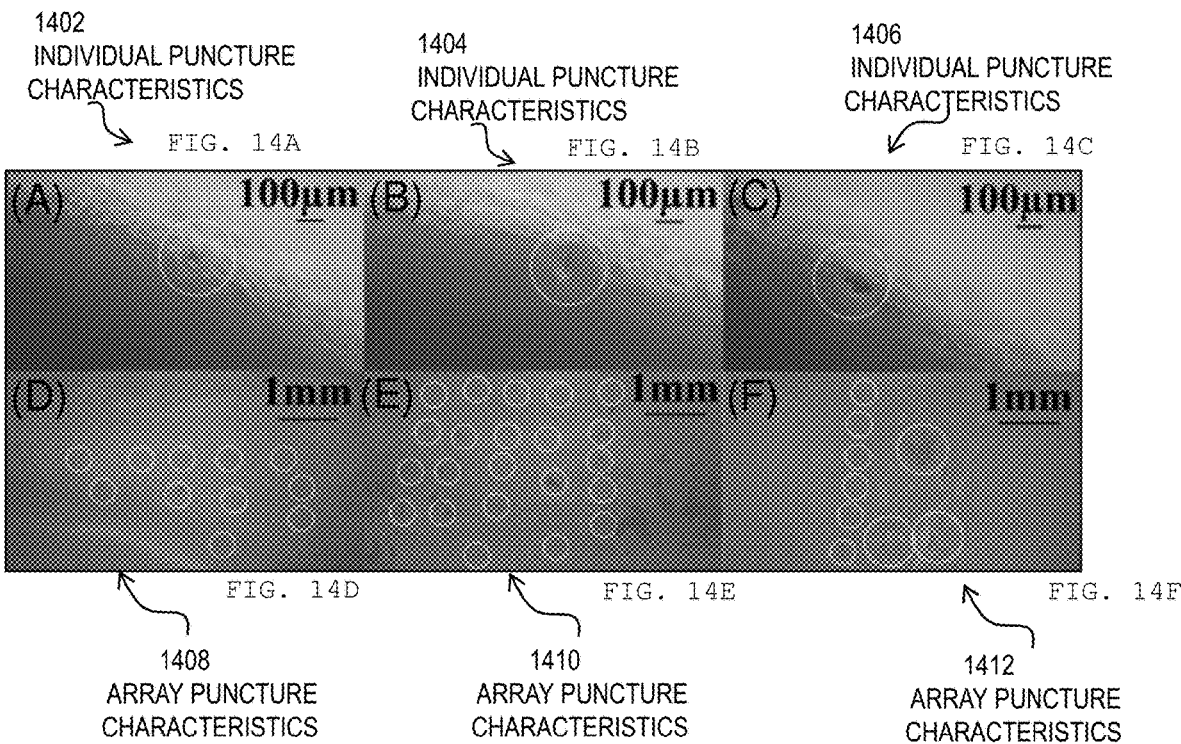
1402 INDIVIDUAL PUNCTURE CHARACTERISTICS — FIG. 14A
1404 INDIVIDUAL PUNCTURE CHARACTERISTICS — FIG. 14B
1406 INDIVIDUAL PUNCTURE CHARACTERISTICS — FIG. 14C
1408 ARRAY PUNCTURE CHARACTERISTICS — FIG. 14D
1410 ARRAY PUNCTURE CHARACTERISTICS — FIG. 14E
1412 ARRAY PUNCTURE CHARACTERISTICS — FIG. 14F
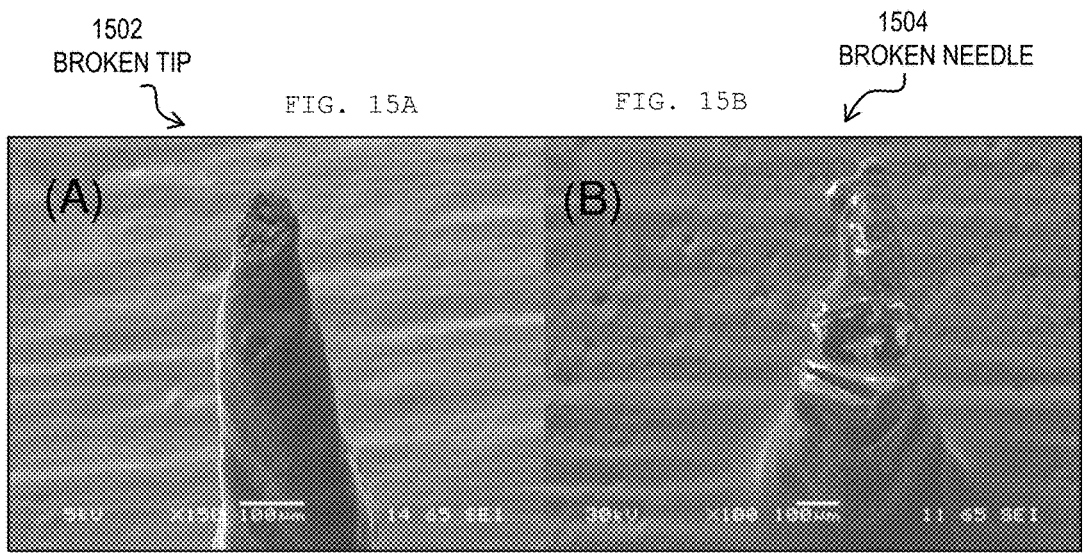
1502 BROKEN TIP — FIG. 15A
1504 BROKEN NEEDLE — FIG. 15B

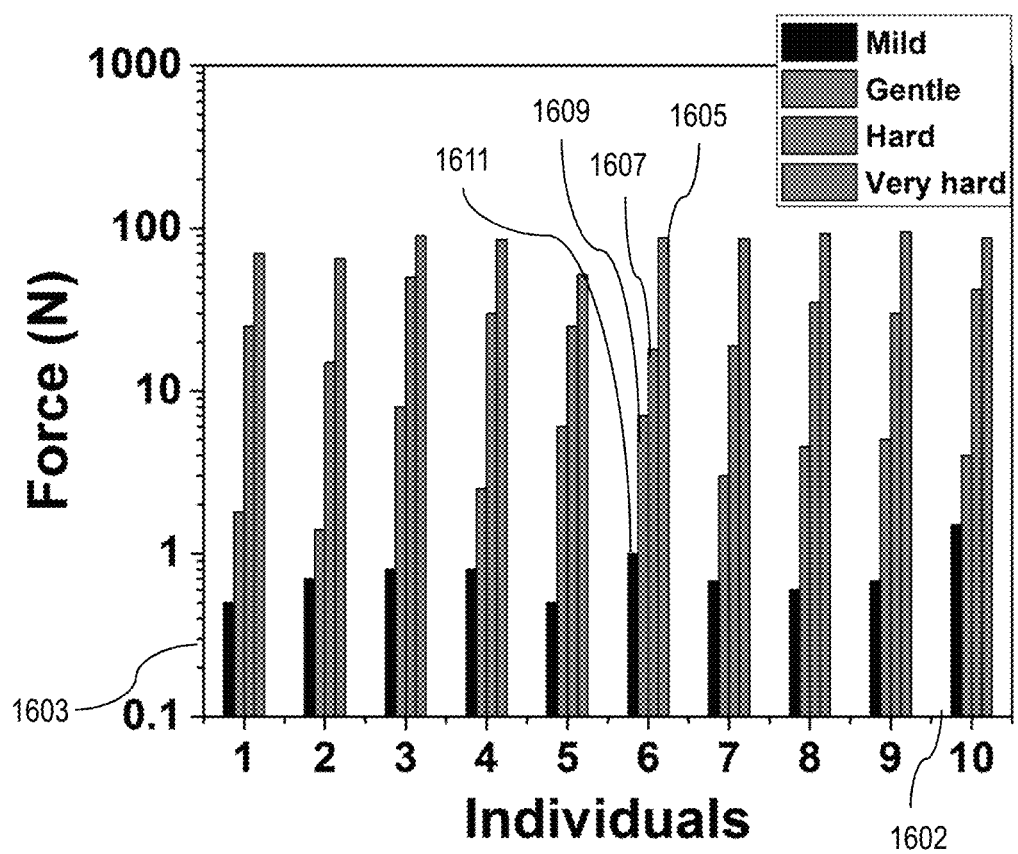

1702
Y-CHANNEL
MICROFLUIDIC DEVICE

1714
MICROFLUIDIC DEVICE

1716 VIA
1718 CHANNEL
1716 VIA
1720 CHANNEL

SYSTEM AND METHOD FOR FORMING A BIOLOGICAL MICRODEVICE

BACKGROUND

Traditional cleanroom techniques involving silicon and glass based technologies have been used to manufacture biological microdevices including microelectrode arrays (MEA), microneedles (MN) and microfluidic (MF) devices. These techniques routinely involve complex design, expensive lithography mask fabrication and semiconductor fabrication process steps with hyper filtered air and expensive instrumentation.

SUMMARY

It is here recognized that conventional cleanroom techniques used to manufacture biological microdevices are deficient for rapid prototyping, since they require complex mask design, expensive equipment and long delays (e.g. 3-4 months) from design to final product. An advantage of the system and method for forming biological microdevices described herein is that it overcomes these drawbacks by facilitating rapid design, utilizing inexpensive equipment (e.g. makerspace and benchtop technologies) and results in a much shorter time window (e.g. 1-3 days) from design to final product. Additionally, another advantage of the system and method described herein is much lower cost (e.g. 10%) for manufacturing each biological microdevice.

In a first set of embodiments, a method is provided for forming a biological microdevice. The method includes applying a biocompatible coarse scale additive process with an additive device and a biocompatible material to form an object. The coarse scale is a dimension not less than about 100 μm. The method also includes applying a biocompatible fine scale subtractive process with a subtractive device to the object. The fine scale is a dimension not greater than about 1000 μm. The method also includes moving the object between the additive device and the subtractive device.

In a second set of embodiments, a system is provided for forming a biological microdevice. The system includes one or more additive devices, a biocompatible material and one or more subtractive devices. The system also includes a means for transporting an object between the additive device and the subtractive device. Additionally, the system includes a processor and a memory including a sequence of instructions. The memory and the sequences of instructions, along with the processor, causes the apparatus to apply a biocompatible coarse scale additive process to form the object, where the coarse scale is a dimension not less than about 100 μm. The memory and the sequences of instructions, along with the processor, causes the apparatus to apply a biocompatible fine scale subtractive process to the object, where the fine scale is a dimension not greater than about 1000 μm. The memory and the sequences of instructions, along with the processor, causes the apparatus to move the object between the additive device and the subtractive device.

In a third set of embodiments, a microelectrode array (MEA) is provided including one or more of a diameter in a range from about 1 μm to about 150 μm, an average 1 kHz impedance in a range from about 20 kΩ to about 200 kΩ and a double layer capacitance of less than about 10 μF.

In a fourth set of embodiments, a microfluidic (MF) device is provided including one or more of a channel with a width in a range from about 50 μm to about 200 μm, a channel with a depth in a range from about 50 μm to about 200 μm and a microfluidic via with a diameter in a range from about 100 μm to about 500 μm.

In a fifth set of embodiments, a method is provided for forming a biological microdevice. The method includes 3D printing a base of an object with a 3D printer and a biocompatible material. The 3D printing is performed using an optical signal oriented at an angle with respect to a surface of the biocompatible material, such that the angle is in a range from about 30 degrees to about 60 degrees.

In a sixth set of embodiments, a microneedle (MN) is provided including a tip with a radius of curvature in a range from about 5 μm to about 100 μm; an aspect ratio defined as a ratio of a height to a diameter of the MN in a range from about 1 to about 10; and a mechanical fracture strength of about 40 N.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 1A is a block diagram that illustrates an example system for forming a biological microdevice, according to an embodiment;

FIGS. 3B and 3C are images that illustrate an example of objects formed by the system of FIG. 1A, according to an embodiment;

FIG. 3D is an image that illustrates an example of a microneedle (MN) array formed by the system of FIG. 1A, according to an embodiment;

FIG. 3E is an image that illustrates an example of a microfluidic (MF) device formed by the system of FIG. 1A, according to an embodiment;

FIG. 3F is an image that illustrates an example of a microelectrode array (MEA) formed by the system of FIG. 1A, according to an embodiment;

FIGS. 4A-4D are images that illustrate an example of a MEA base printed by the 3D printer of FIG. 1A at different angles, according to an embodiment;

FIGS. 4E-4H are images that illustrate an example of a MN printed by the 3D printer of FIG. 1A at different angles, according to an embodiment;

FIG. 5A is an image that illustrates an example of the laser of the 3D printer of FIG. 1B oriented at 90 degrees relative to the printed object, according to an embodiment;

FIG. 5B is an image that illustrates an example of the laser and undesired curing locations along the printed object of FIG. 5A, according to an embodiment;

FIG. 5C is an image that illustrates an example of the laser of the 3D printer of FIG. 1B oriented at 0 degrees relative to the printed object, according to an embodiment;

FIG. 5D is an image that illustrates an example of the laser and undesired curing locations along the printed object of FIG. 5C, according to an embodiment;

FIG. 5E is an image that illustrates an example of an intensity profile of the optical signal of FIG. 5A, according to an embodiment;

FIG. 7C is a plot that illustrates an example of average impedance of a formed MEA over a full frequency spectrum using the system of FIG. 1A, according to an embodiment;

FIG. 7F is a plot that illustrates an example of a current-scan rate of a formed MEA using the system of FIG. 1A before and after electroless plating, according to an embodiment;

FIGS. 8A-8D are images that illustrate an example of a microelectrode array (MEA) formed using the system of FIG. 1A during various stages of electroless plating, according to an embodiment;

FIG. 10 is a plot that illustrates an example of full spectrum impedance of a formed MEA using the system of FIG. 1A, according to an embodiment;

FIG. 11A is an image that illustrates an example of a MN formed using the system of FIG. 1A without temperature curing, according to an embodiment;

FIG. 11B is an image illustrates an example of a MN formed using the system of FIG. 1A with temperature curing, according to an embodiment;

FIGS. 12A-12D are images that illustrate an example of a microneedle (MN) formed using the system of FIG. 1A with various stages of acetone vapor polishing, according to an embodiment;

FIGS. 14A-14C are images that illustrate an example of puncture characteristics of an individual microneedle (MN) along the skin using different forces, according to an embodiment;

FIGS. 14D-14F are images that illustrate an example of puncture characteristics of a microneedle (MN) array along the skin using different forces, according to an embodiment;

FIG. 15A is an image illustrates an example of a MN formed using the system of FIG. 1A with tip breakage observed with an imposed force, according to an embodiment;

FIG. 15B is an image illustrates an example of a MN formed using the system of FIG. 1A with complete breakage observed with an imposed force, according to an embodiment;

FIG. 16 is a plot that illustrates an example of a qualitative assessment of multiple puncture forces imposed on a plurality of individuals;

FIG. 21 is a block diagram that illustrates a mobile terminal upon which an embodiment of the invention may be implemented.

DETAILED DESCRIPTION

Figure 1B:
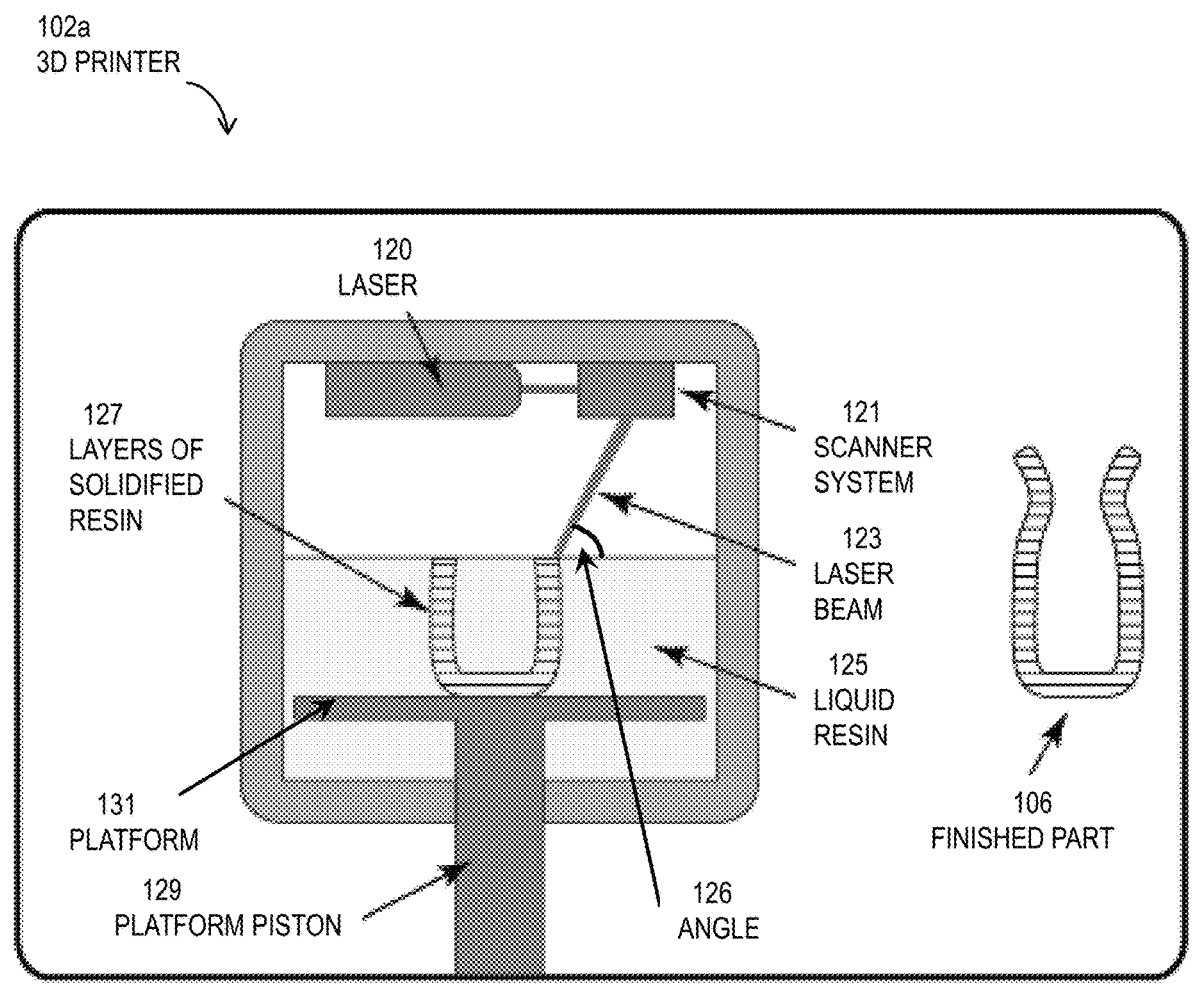
FIG. 1B is an image that illustrates an example of a 3D printer of the system of FIG. 1A, according to an embodiment.

A method and apparatus are described for forming a biological microdevice. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about ×" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of a system and method for forming a biological microdevice or a lab on-a-chip device, including miniaturized biological devices, biosensors and bioactuators. In an embodiment, a biological microdevice is defined as a device fabricated with micro or nanotechnologies that is capable of performing assays with biological agents outside the body (e.g. in vitro), on the body (e.g. wearable) or inside the body (e.g. implantable). In an embodiment, the invention is directed to a system and method for forming a microelectrode array (MEA). In some embodiments, the invention is directed to a system and method for forming a MEA targeted at in-vitro neural and cardiac electrophysiology. In other embodiments, the invention is directed to a system and method for forming a microfluidic (MF) device. In an embodiment, the invention is directed to a system and method for forming a multi-layer MF chip targeted at multiplexed assays utilized in in-vitro cell, tissue and scaffolding applications. In yet other embodiments, the invention is directed to a system and method for forming a microneedle (MN) array targeted at drug delivery through a transdermal route. In an embodiment, the microdevices that are formed by the system and method herein can be used in a variety of applications including drug screening, drug delivery, toxicity testing, pharmacological assays, agricultural compound testing, label-free assays and genomic testing in a commercial setting. However, the invention is not limited to these contexts. In other embodiments, the system and method can be used to form other devices including cantilevers, impedance sensors, magnetic sensors, strain sensors and microtools which can be used in other biosensing and biological micromanipulation applications. In still yet other embodiments, the system and method can be used to form other devices including implantable devices, bioelectronics devices, microreactors, micromixers, oil recovery, energy harvesters, organ on a chip or disease in a dish models.

1. OVERVIEW

FIG. 1A is a block diagram that illustrates an example system 100 for forming a biological microdevice, according to an embodiment. In an embodiment, the system 100 includes an additive device 102 and biocompatible material that apply a biocompatible coarse scale additive process to form an object 106. In one embodiment, the coarse scale is a dimension not less than about 100 μm. In another embodiment, the coarse scale is a dimension not less than about 100 nanometers (nm). In some embodiments, advantages of such a lower limit on the coarse scale dimension of the additive process include but are not limited to improved sensitivity of the assay; small device size; better selectivity of the device; integration with Complementary Metal-Oxide-Semiconductor (CMOS) electronics for on-chip detection and sensing portability; and in field detection and sensing.

Once the object 106 is formed, the system 100 also includes a means for moving the object 106 from the additive device 102 to a subtractive device 104. In various embodiments, the means is a conveyor belt 108 or autonomous vehicle or some combination. In an embodiment, the means is automated robotics. In other embodiments, the means involves manually moving the object 106 from the additive device 102 to the subtractive device 104.

In some embodiments, the subtractive device 104 applies a biocompatible fine scale subtractive process to the object 106 until a final end product (e.g. biological microdevice) is formed. In some embodiments, the fine scale is a dimension not greater than about 100 μm. In other embodiments, the fine scale is a dimension not greater than 1000 microns. In some embodiments, advantages of such an upper limit on the fine scale dimension of the subtractive process include but are not limited to easier microfabrication; easier assembly; easy translation to manufacturing; and faster time to market. In some embodiments, a desired scale of the final end product is less than the coarse scale of the additive process and is greater than the fine scale of the subtractive process. In one embodiment, the desired scale of the final end product is in a range from about 10 μm to about 1000 μm. In an example embodiment, the desired scale of the final end product is greater than the coarse scale of the additive process and thus the final end product can be formed without the fine scale subtractive process.

In some embodiments, multiple additive devices 102 apply multiple biocompatible coarse scale additive processes using multiple biocompatible materials to form the object 106. In an embodiment, a first additive device 102 and first biocompatible material apply a first biocompatible coarse scale additive process to form a base of the object 106 and a second additive device 102 and second biocompatible material apply a second biocompatible coarse scale additive process to form a layer on the base of the object 106. In another embodiment, a dimension of the first coarse scale process is greater than a dimension of the second coarse scale process. In some of these embodiments, the conveyor belt 108 is used to move the object 106 from the first additive device 102 to the second additive device 102.

In other embodiments, multiple subtractive devices 104 apply multiple biocompatible fine scale subtractive processes to the object 106. In an embodiment, a first subtractive device 104 applies a first biocompatible fine scale subtractive process to the object 106 and a second subtractive device 104 applies a second biocompatible fine scale subtractive process to the object 106. In another embodiment, a dimension of the first fine scale process is greater than a dimension of the second fine scale process. In some of these embodiments, the conveyor belt 108 is used to move the object 106 from the first subtractive device 104 to the second subtractive device 104.

In some embodiments, one or more additive devices 102 apply biocompatible coarse scale additive processes to form a base of the object 106. In an embodiment, the additive device 102 is a processing tool, such as a 3D printer 102a. In an embodiment, 3D printing is a process in which the biocompatible material is joined or solidified under computer control to create the base of the object 106, with material being added together (such as liquid molecules or powder grains being fused together). Various types of 3D printing are available. The main differences between processes are in the way layers are deposited to create the base of the object 106 and in the materials that are used. Some methods melt or soften the material to produce the layers, for example selective laser melting (SLM) or direct metal laser sintering (DMLS), selective laser sintering (SLS), fused deposition modeling (FDM), or fused filament fabrication (FFF), while others cure liquid materials using different sophisticated technologies, such as stereolithography (SLA). With laminated object manufacturing (LOM), thin layers are cut to shape and joined together (e.g., paper, polymer, metal).

FIG. 1B is an image that illustrates an example of the 3D printer 102a of the system 100 of FIG. 1A, according to an embodiment. In an embodiment, the 3D printer 102a employs stereolithography (SLA) as an additive manufacturing process that works by focusing an ultraviolet (UV) laser 120 onto a vat of photopolymer liquid resin 125 using a scanner system 121. In an embodiment, the scanner system 121 includes one or more mirrors and/or lenses that direct the laser beam 123 such that it is oriented at a selective angle 126 with respect to a surface of the liquid resin 125. With the help of computer aided manufacturing or computer aided design (CAM/CAD) software, the UV laser 123 is used to draw a pre-programmed design or shape onto the surface of the photopolymer resin 125. Since photopolymer resins 125 are sensitive to ultraviolet light, the resin 125 is photochemically solidified and forms a single layer 127 of the desired base of the object 106. A build platform 131 and platform piston 129 are then lowered one layer 127 and a blade recoats the top of the tank with resin 125. This process is repeated for each layer 127 of the design until the base of the object 106 is complete. In other embodiments of the 3D printer 102a, the laser 120 is positioned below the vat of resin 125 is transmitted through a transparent window at a base of the vat of the resin 125 so to form each layer 127 of the object 106 at the base of the vat of resin 125, while the platform 131 rises upward in between the formation of each layer 127.

FIG. 5A is an image that illustrates an example of the laser 123 of the 3D printer 102a of FIG. 1B oriented such that the angle 126 is at about 90 degrees relative to the surface of the liquid resin 125, according to an embodiment. FIG. 5B is an image that illustrates an example of the laser 123 and undesired curing locations 512 along the printed base of the object 106 of FIG. 5A, according to an embodiment. In one embodiment, FIG. 5B depicts that when the angle 126 of the laser beam 123 is about 90 degrees, the curing or solidifying of the liquid resin 125 is not contained to the diameter of the laser beam 123 and consequently the dimension of the coarse scale of the 3D printing is not optimized when the angle 126 is about 90 degrees.

FIG. 5C is an image that illustrates an example of the laser 123 of the 3D printer 102a of FIG. 1B oriented such that the angle 126 is at about 0 degrees relative to the surface of the liquid resin 125, according to an embodiment. FIG. 5D is an image that illustrates an example of the laser 123 and undesired curing locations 512 along the printed base of the object 106 of FIG. 5C, according to an embodiment. In one embodiment, FIG. 5D depicts that when the angle 126 of the laser beam 123 is about 0 degrees, the curing or solidifying of the liquid resin 125 is not contained to the diameter of the laser beam 123 and consequently the dimension of the coarse scale of the 3D printing is not optimized when the angle 126 is about 0 degrees. FIG. 5E is an image that illustrates an example of an intensity profile 514 of the laser 123 of FIG. 5A, according to an embodiment. FIG. 5E depicts that the undesired curing locations 512 reside outside the full width half maximum (FWHM) of the intensity profile 514 of the laser beam 123. In an embodiment, the undesired curing locations 512 are due to diffraction of the laser 123 when the angle 126 is about 90 degrees.

Based on the data presented in FIGS. 5A-5D, the dimension of the coarse scale of the 3D printer 102a is not optimized when the angle 126 is about 0 degrees or about 90 degrees. Therefore it is advantageous when the angle 126 is in a range from about 30 degrees to about 60 degrees to reduce the size of undesired curing. In an embodiment, the dimension of the coarse scale of the 3D printing is not less than about 100 µm. In one embodiment, the dimension of the coarse scale of the 3D printing is about 140 µm. In another embodiment, where 3D printing involves 2 photon photopolymerization technology, the dimension of the coarse scale is not less than about 100 nanometers (nm).

In some embodiments, in addition to the 3D printer 102a, other additive devices 102 are used to form the base of the object 106. In an embodiment, the additive device 102 is a processing tool such as a heater 102d that is used to cure the base of the object 106 after it is printed by the 3D printer 102a. The heater 102d cures the base of the object 106 at a selective temperature for a selective time. In an example embodiment, the heater 102d is a PR305225M® made by Thermo Fisher Scientific, Waltham, Mass. In some embodiments, the base of the object 106 is not temperature cured using the heater 102d. Additionally, in another embodiment, the base of the object 106 is rinsed with a solution (e.g. isopropyl alcohol) after it is cured with the heater 102d. In an embodiment, the rinsing with the solution involves a solvent bath, solvent sonication and ultrasonic agitation. A two-step cleaning of the base of the object 106 is performed in an isopropyl alcohol bath. The base of the object 106 is rinsed in the first bath for 10 minutes followed by rinsing in the second bath for another 10 minutes. In an embodiment, the additive device 102 is a processing tool such as a nitrogen gun 102g that is used to dry the base of the object 106 after it is printed by the 3D printer 102a. In an example embodiment, the nitrogen gun 102g should have no noticeable impact on the dimensional scale of the base object 106. In an example embodiment, the nitrogen gun 102g is provided by VWR, Radnor, Pa.

In some embodiments, after the base of the object 106 is formed, one or more additive devices 102 are used to form a conductive layer on the base of the object 106. In an embodiment, the additive device 102 includes a processing tool such as a cotton swab 102f that is used to coat conductive ink over the surface of the base of the object 106. In some embodiments, forming of the conductive layer using the swab 102f can achieve a coarse scale resolution as low as about 50 µm. In other embodiments, optimizing this technique and perhaps automating can achieve lower resolutions (e.g. ~5 µm).

In still other embodiments, the dimensional scale of the base of the object 106 is retained within ±5% after forming the conductive layer. In an embodiment, the heater 102d is used to cure the coated object 106 at a selective temperature for a selective time. In yet another embodiment, the coated object 106 is rinsed with a solution (e.g. isopropyl alcohol). In yet another embodiment, the additive device 102 includes the nitrogen gun 102g and the coated object 106 is dried with the nitrogen gun 102g.

In some embodiments, after the 3D printer 102a forms the base of the object 106, one or more additive devices 102 are used to form an insulation layer on the base of the object 106. In some embodiments, a thickness of the insulation layer can be as low as about 100 nm (e.g. parylene vapor deposition) depending on the technology used. In other embodiments, after the conductive layer is formed on the base of the object 106, one or more additive devices 102 are used to form the insulation layer on the conductive layer of the object 106. In an embodiment, the additive device 102 includes a processing tool such as a cutting device 102h (e.g. scissors) to cut an insulation layer to a desired size based on dimensions of the object 106. In an embodiment, the insulation layer is an adhesive layer including a liner that is removed so that the adhesive layer can be affixed to the base of the object 106. In another embodiment, the additive device 102 includes a processing tool such as a laminating press 102b that presses the insulation layer against the base of the object 106 with a specified force for a specified time. In an example embodiment, a thickness of the insulation layer is about 60 µm after being pressed using the laminating press 102b. In one embodiment, the dimensional scale of the base of the object 106 is retained within ±5% after forming the insulation layer.

In some embodiments, after the 3D printer 102a forms the base of the object 106, one or more additive devices 102 are used to form a thin insulation layer on the base of the object 106. In an embodiment, the additive device 102 includes a processing tool such as a spin coater 102 to perform a biocompatible additive spin coating process, in which a photoresist is applied to the surface of the base of the object 106 after which the base of the object 106 is inserted into the spin coater 102c. In one embodiment, the spin coater 102c is operated at a specific rotation speed for a specific time. In an embodiment, after spin coating the base of the object 106, the base of the object 106 is positioned in the heater 102d and cured for a specific temperature and a specific time, after which the base of the object 106 is exposed to ultraviolet (UV) radiation from a UV lamp 102e for a specific time. In some embodiments, the base of the object 106 is cured in the heater 102d for a second time after the UV exposure.

In some embodiments, after the recording sites are formed in the insulation layer of the object 106 by the subtractive device 104, an additive device 102 is used to deposit a solution over the recording sites. In an embodiment, the additive device 102 is a processing tool such as a transfer pipette 102i that is used to transfer a solution of microelectrode material (e.g. porous platinum) and deposit the solution over the recording sites for a predetermined time period (e.g. 6 hours).

In some embodiments, the subtractive device 104 is used to perform the fine scale subtractive process on the object 106. In an example embodiment, the subtractive device 104 is used to perform the fine scale subtractive process on the insulation layer of the object 106. In one embodiment, the subtractive device 104 is a processing tool such as a laser 104a that is used to fabricate one or more recording sites on the formed insulation layer of the object 106. In an example embodiment, the laser 104a has a spot size of about 70 µm×50 µm. In some of these embodiments, the fine scale of the subtractive process using the laser 104a has a dimension not greater than about 70 µm. In another example embodiment, the laser 104a has a spot size of about 30 µm×30 µm. In some of these embodiments, the fine scale of the subtractive process using the laser 104 has a dimension not greater than about 30 µm. In still other embodiments, the fine scale of the subtractive process using the laser 104 has a dimension with a resolution of about 1 µm.

In one embodiment, the subtractive device 104 is a processing tool such as a drill bit 104b that is used to perform the fine scale subtractive process on the object 106. In one embodiment, the drill bit 104b is used to fabricate one or more recording sites on the formed insulation layer of the object 106. In an example embodiment, the drill bit 104b has a diameter in a range from about 200 µm to about 300 µm. In this example embodiment, the fine scale of the subtractive process using the drill bit 104b has a diameter of about 210 µm. In another example embodiment, the fine scale of the subtractive process using the drill bit 104b has a diameter of about 7 µm or in a range from about 7 µm to about 300 µm.

In some embodiments, the subtractive device 104 is used to polish a surface of the object 106. In an embodiment, the subtractive device 104 includes a processing tool such as a glass beaker 104c in which acetone soaked wipes are hung from the interior of the glass beaker 104c. In an embodiment, the base of the object 106 is positioned within the acetone vapor filled glass beaker 104c and the glass beaker 104c is sealed for a predetermined time. In an example embodiment, the acetone vapor isotropically etches the material of the object 106 and result in smaller dimensional scale.

Figure 19:
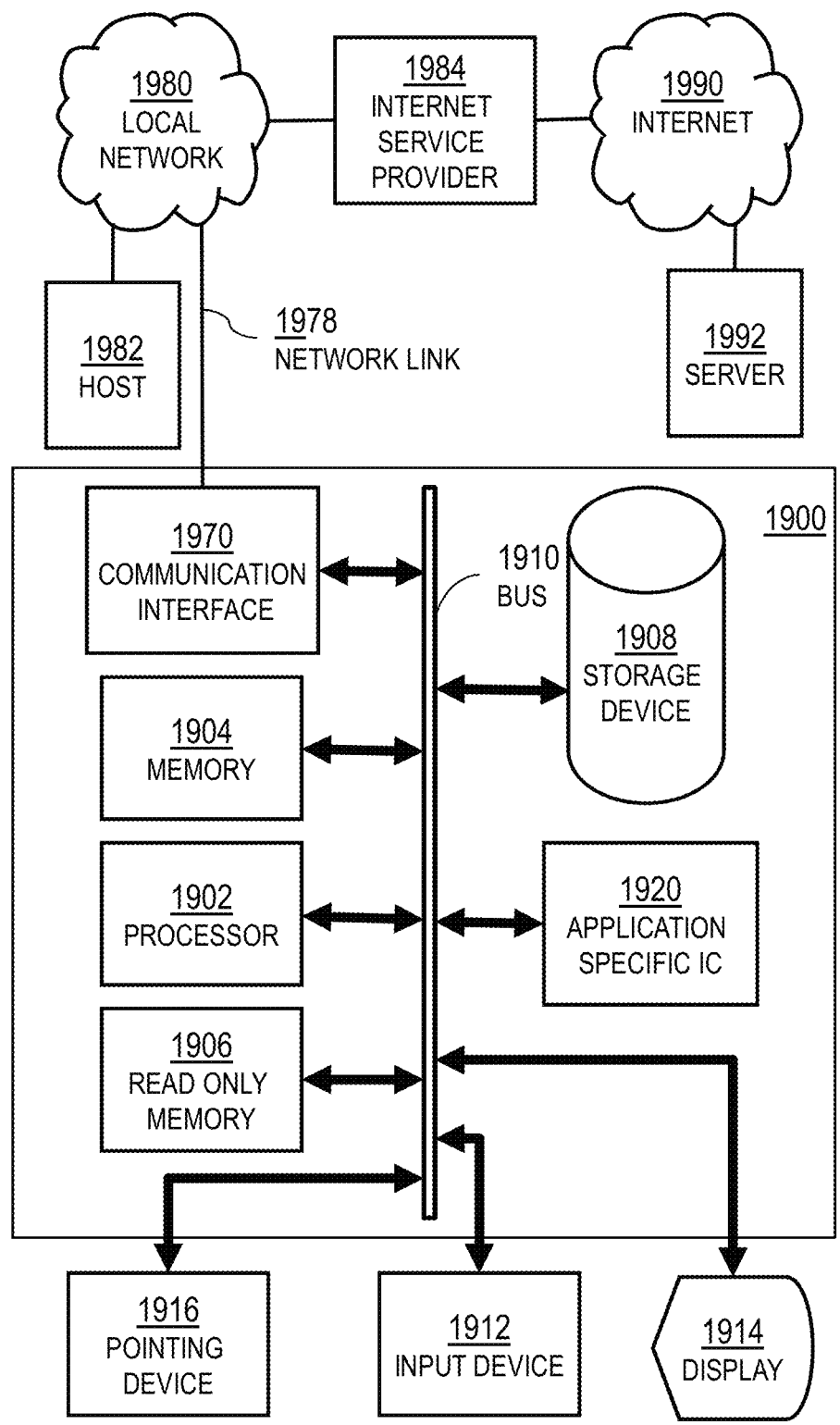
FIG. 19 is a block diagram that illustrates a computer system upon which an embodiment of the invention may be implemented.
Figure 20:
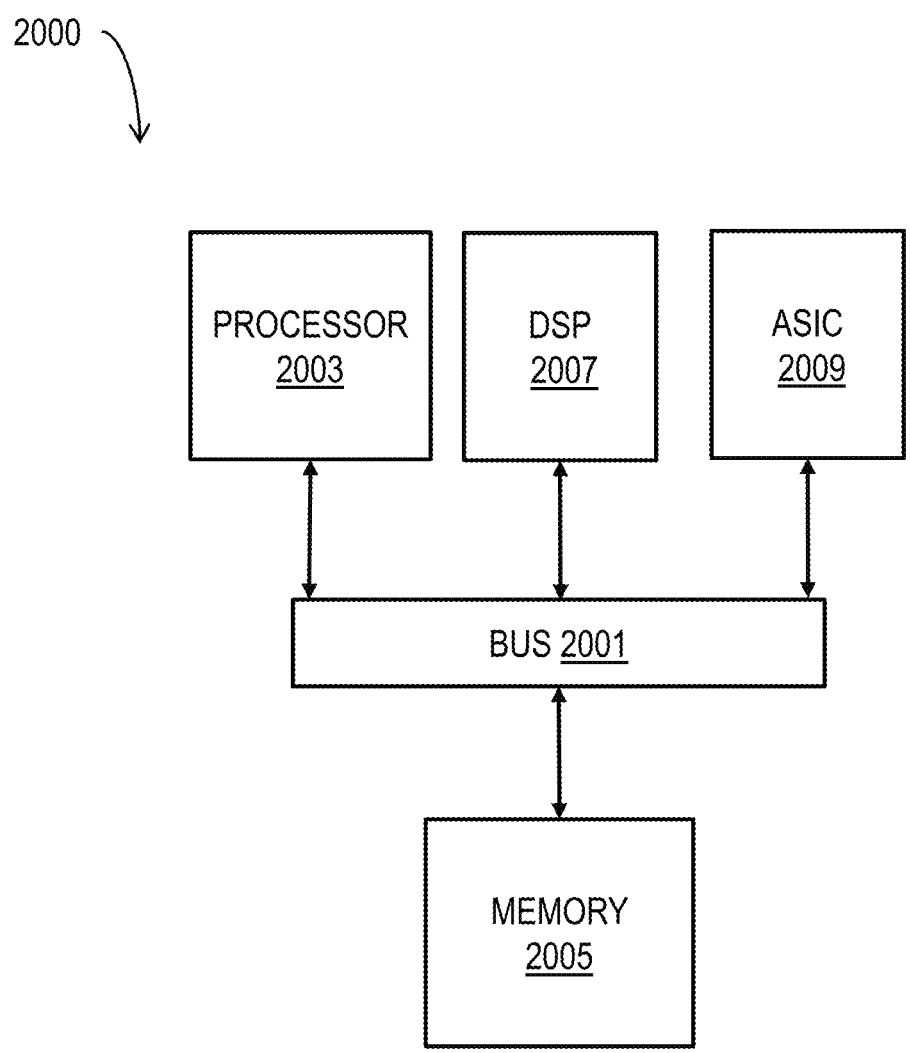
FIG. 20 is a block diagram that illustrates a chip set upon which an embodiment of the invention may be implemented.

As illustrated in FIG. 1A, the processor 110 is configured to control operation of each additive device 102 and subtractive device 104 as well as control the conveyor belt 108 or autonomous vehicle to move the object 106 from the additive device 102 to the subtractive device 104, from the subtractive device 104 to the additive device 102, among the additive devices 102 and among the subtractive devices 104. The processor 110 includes a biological microdevice forming process module 111 to perform one or more steps of a method described below with reference to FIG. 2. In various embodiments, the processor 110 comprises one or more general purpose computer systems, as depicted in FIG. 19 or one or more chip sets as depicted in FIG. 20 or one or more mobile terminals as depicted in FIG. 21, and instructions to cause the computer or chip set or mobile terminal to perform one or more steps of a method described below with reference to FIG. 2.

Figure 2:
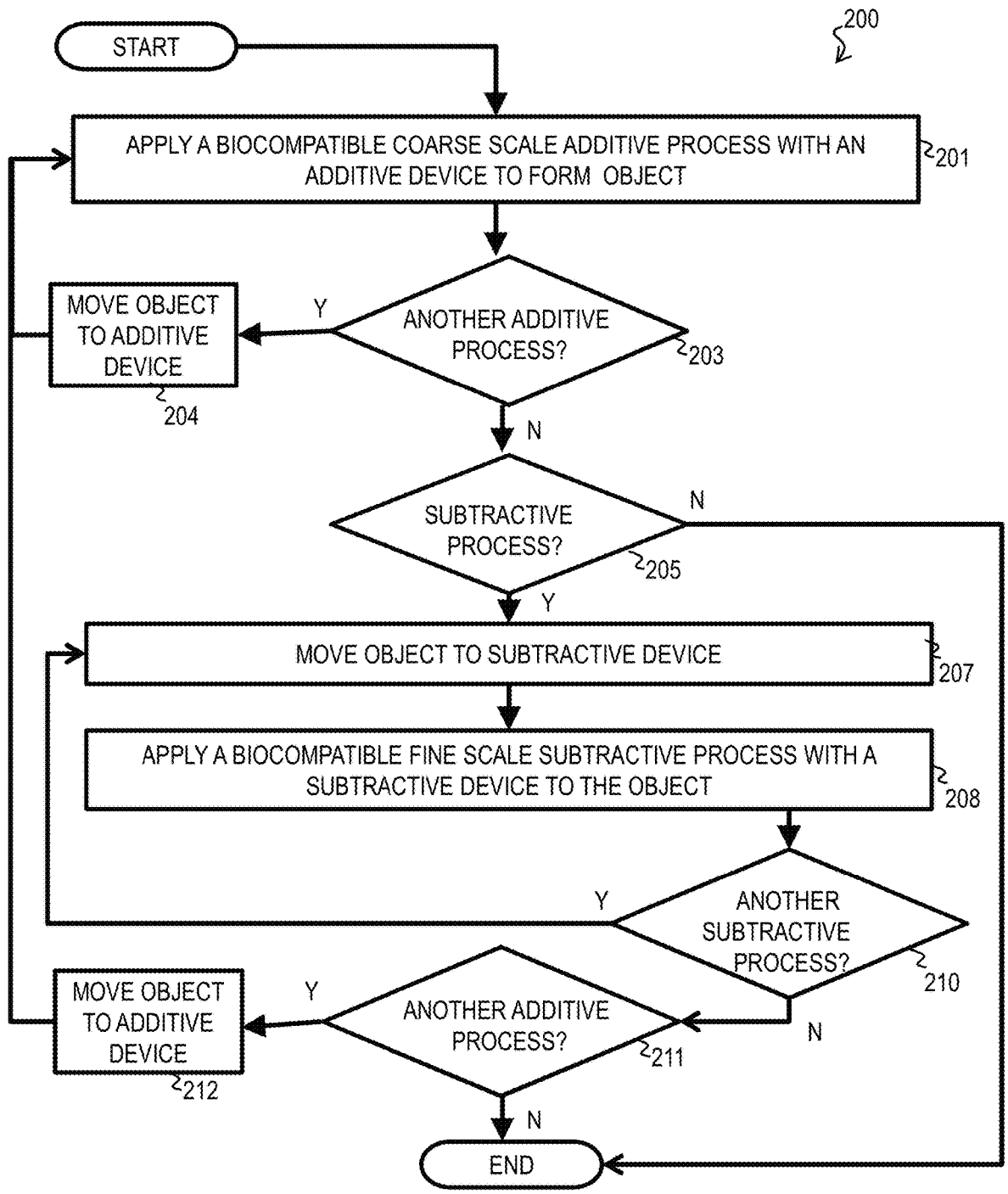
FIG. 2 is a flow diagram that illustrates an example of a method for forming a biological microdevice, according to an embodiment.

FIG. 2 is a flow diagram that illustrates an example of a method 200 for forming a biological microdevice, according to an embodiment. Although steps are depicted in FIG. 2 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 201, a biocompatible coarse scale additive process is applied with an additive device 102 to form at least a part of the object 106. In some embodiments, in step 201 the 3D printer 102a is used to form a base of the object 106. In an embodiment, in step 201 the 3D printer 102a is operated such that the angle 126 of the laser 123 is adjusted within the range from about 30 degrees to about 60 degrees. In an embodiment, the coarse scale has a dimension that is not less than about 100 µm. In an embodiment, in step 201 a file (e.g. CAD file) including a design of the base of the object 106 is uploaded to a memory of the processor 110. In another embodiment, an input device 1912 (e.g. keyboard) and/or pointing device 1916 (e.g. mouse) of the computer system is used in conjunction with design software on the computer system to generate the file (e.g. CAD file) of the design of the base of the object 106 and the file is transferred to the memory of the processor 110. In an example embodiment, the file includes the shape and dimension of each layer 127 of the object 106. In an embodiment, the processor 110 controls the operation of the laser 123 and movement of the platform 131 to form each layer 127 of the object 106 based on the file in the memory.

In some embodiments, in step 201 the base of the object 106 printed by the 3D printer 102a is inserted into the heater 102d and cured at a specific temperature for a specific time period. In other embodiments, in step 201 the base of the object 106 printed by the 3D printer 102*a* is not cured with the heater 102*d*. In another embodiment, in step 201 the base of the object 106 printed by the 3D printer 102*a* is rinsed with a solution (e.g. isopropyl alcohol) after it is cured by the heater 102*d*. In another embodiment, in step 201 the nitrogen gun 102*g* is used to dry the base of the object 106 after it is printed by the 3D printer 102*a*.

After the base of the object 106 is formed in step 201, the method 200 passes to step 203 to determine whether additional additive processes are to be performed to form the biological microdevice. If additional additive processes are to be performed next, the method 200 moves to step 204 where the base of the object 106 is moved to one or more additive devices 102. The method 200 then moves back to step 201 to perform the additional additive process.

In another embodiment, the method 200 moves through step 204 and back to step 201 to form a conductive layer on the base of the object 106. In one embodiment, this step is performed to define the traces and conductive contact pads of a microelectrode array (MEA). In this iteration of step 201, the cotton swab 102*f* is used to coat conductive ink over the surface of the base of the object 106. In another embodiment, the heater 102*d* is used to cure the coated object 106 at a selective temperature for a selective time. In yet another embodiment, in this iteration of step 201, the coated object 106 is rinsed with the solution (e.g. isopropyl alcohol) and is subsequently dried with the nitrogen gun 102*g*.

In another embodiment, the method 200 moves through step 204 and back to step 201 to form the insulation layer on the base of the object 106. In one embodiment, this step is performed to define the insulation layer of the MEA or a microfluidic (MF) device. In this iteration of step 201, the cutting device 102*h* is used to cut the insulation layer to the desired size based on dimensions of the object 106. In another embodiment, the adhesive layer is affixed to the base of the object 106 and the laminating press 102*b* presses the insulation layer against the base of the object 106 with the specified force for the specified time.

In another embodiment, the method 200 moves through step 204 and back to step 201 to form the thin insulation layer on the base of the object 106. In one embodiment, this step is performed to define the thin insulation layer of the MEA or a microfluidic (MF) device. In this iteration of step 201, a biocompatible additive spin coating is performed where the photoresist is applied to the surface of the base of the object 106 and the base of the object 106 is inserted into the spin coater 102*c*. The spin coater 102 is then operated at a specific rotation speed for a specific time. In an embodiment, the base of the object 106 is then positioned in the heater 102*d* and cured for a specific temperature over a specific time, after which the base of the object 106 is exposed to UV radiation from the UV lamp 102*e*. In an embodiment, the base of the object 106 is cured in the heater 102*d* for a second time after the UV exposure.

After the second iteration of step 201, the method 200 passes to step 203 to determine whether additional coarse scale additive processes are to be performed to form the biological microdevice. If additional coarse scale additive processes are still to be performed next, the method 200 moves to step 204 where the base of the object 106 is moved to one or more additive devices 102. The method 200 then moves back to step 201 to perform the additional coarse scale additive process. In an embodiment, when forming the MEA the method 200 prints the base of the object 106 with the 3D printer 102*a* during the first iteration of step 201, forms the conductive layer on the base of the object 106 during a second iteration of step 201 and forms the insulation layer on the base of the object 106 during a third iteration of step 201.

If it is determined in step 203 that additional coarse scale additive processes are not to be performed next, then the method 200 moves to step 205, where it is determined whether fine scale subtractive processes are to be performed next. In some embodiments, where the method 200 is used to form the microfluidic (MF) device or the microneedle (MN), fine scale subtractive processes are not to be performed and thus the method 200 ends. In other embodiments, where the method 200 is used to form the microfluidic (MF) device, one or more fine scale subtractive processes may be performed and thus the method 200 passes from step 205 to step 207. In still other embodiments, where the method 200 is used to form the microneedle (MN), one or more fine scale subtractive processes may be performed and thus the method 200 passes from step 205 to step 207. At step 207, the object 106 is moved from the additive device 102 to the subtractive device 104 to perform the fine scale subtractive process. In one embodiment, in step 207 the conveyor belt 108 or autonomous vehicle moves the object 106 from the additive device 102 to the subtractive device 104.

In some embodiments, in step 208 a biocompatible fine scale subtractive process is applied to the formed object 106 with the subtractive device 104. In an embodiment, in step 208 the biocompatible fine scale subtractive process is performed on the insulation layer of the object 106 formed in step 201. In some embodiments, the subtractive device 104 is the laser 104*a* and in step 208 the laser 104*a* is used to fabricate one or more recording sites in the formed insulation layer of the object 106. In other embodiments, the subtractive device 104 is the drill bit 104*b* and in step 208 the drill bit 104*b* is used to fabricate one or more recording sites in the formed insulation layer of the object 106. In an embodiment, the one or more recording sites fabricated in step 208 are used to form a MEA device. In still other embodiments, the subtractive device 104 is the vapor filled glass beaker 104*c* that is used to polish a surface of the object 106. In an embodiment, the surface of the object 106 is polished using the vapor filled glass beaker 104*c* to form the microneedle (MN) device. In an example embodiment, the surface of the MN device is polished using the vapor filled glass beaker 104*c* to define a tip of the MN device.

In some embodiments, in step 210 it is determined whether to apply another subtractive process. If so, the object 106 is moved to the next subtractive device 104 in step 207 to perform the next subtractive process in step 208. If no additional subtractive processes are to be applied, control passes to step 211.

In some embodiments, step 211 is performed in a similar manner as step 203. In an embodiment, in step 211 it is determined whether another coarse scale additive process should be performed next to form the biological microdevice. In one embodiment, where the method 200 is used to form a functional MEA and one or more recording sites are fabricated in step 208, in step 211 it is determined that an additional additive process should be performed with the transfer pipette 102*i* to deposit conductive material at the recording sites (e.g. electroless plating of the recording sites). In an embodiment, the method 200 moves to step 212 where the conveyor belt 108 moves the object 106 from the subtractive device 104 to the transfer pipette 102*i*. The method 200 then moves back to step 201 where a coarse scale additive process is performed including preparing a solution of microelectrode material (e.g. porous platinum)

and depositing the solution over the recording sites for a predetermined time period (e.g. 6 hours) using the transfer pipette 102i. The method 200 then proceeds to steps 203, 205, 207, 208, 210, 211, 212 or some combination, which determine when no further additive or subtractive processes are required, thereby ending the method 200 with a formed biological microdevice.

2. EXAMPLE EMBODIMENTS

According to an example embodiment, the system 100 utilizes makerspace fabrication-based technology and utilizes the method 200 to develop and characterize one or more distinct biological microdevices: MEAs, MNs and multi-layer microfluidics by using materials and equipment that present the promise for low cost, highly accessible, simple, scalable, large area manufacturing. The technology involves the use of different additive devices 102 that perform different coarse scale additive processes, including a 3D printing additive process, a selective ink casting additive process and a micromachined lamination additive processes. The selective ink casting additive process is used to form the conductive layer on the base of the object. The lamination additive process using biocompatible adhesives/films forms the insulation layer on the base of the object 106. In some embodiments, both of these layers are built upon the base of the object 106 that is formed by the additive 3D printing process. In one embodiment, the method 200 involves an intimate symbiosis between coarse scale additive processes in step 201 and fine scale subtractive processes in step 208 that enable micron-scale precision. In an embodiment, the desired scale of the formed biological microdevice is less than a coarse scale of the additive processes and is greater than a fine scale of the subtractive processes. As a result, the additive and subtractive processes in the method 200 leverages the rapid, cost effective fabrication advantages of additive technologies to produce arbitrary non-planar shapes and curved faces that would be difficult to obtain utilizing traditional micromachining technologies. The coarse scale additive steps 201 of the method 200 are followed by the use of the advanced precision of fine scale subtractive technologies during the subtractive steps 208 to remove material as needed to produce a myriad of biological microdevices. Such a combined process technology has the power to diversify and consolidate the varied application fields for printed microscale devices thus realizing Micro Total Analysis Systems (MicroTAS) and Biomedical Micro Electro Mechanical Systems (BioMEMS) devices in bio-functional polymers and resins.

Figure 3A:
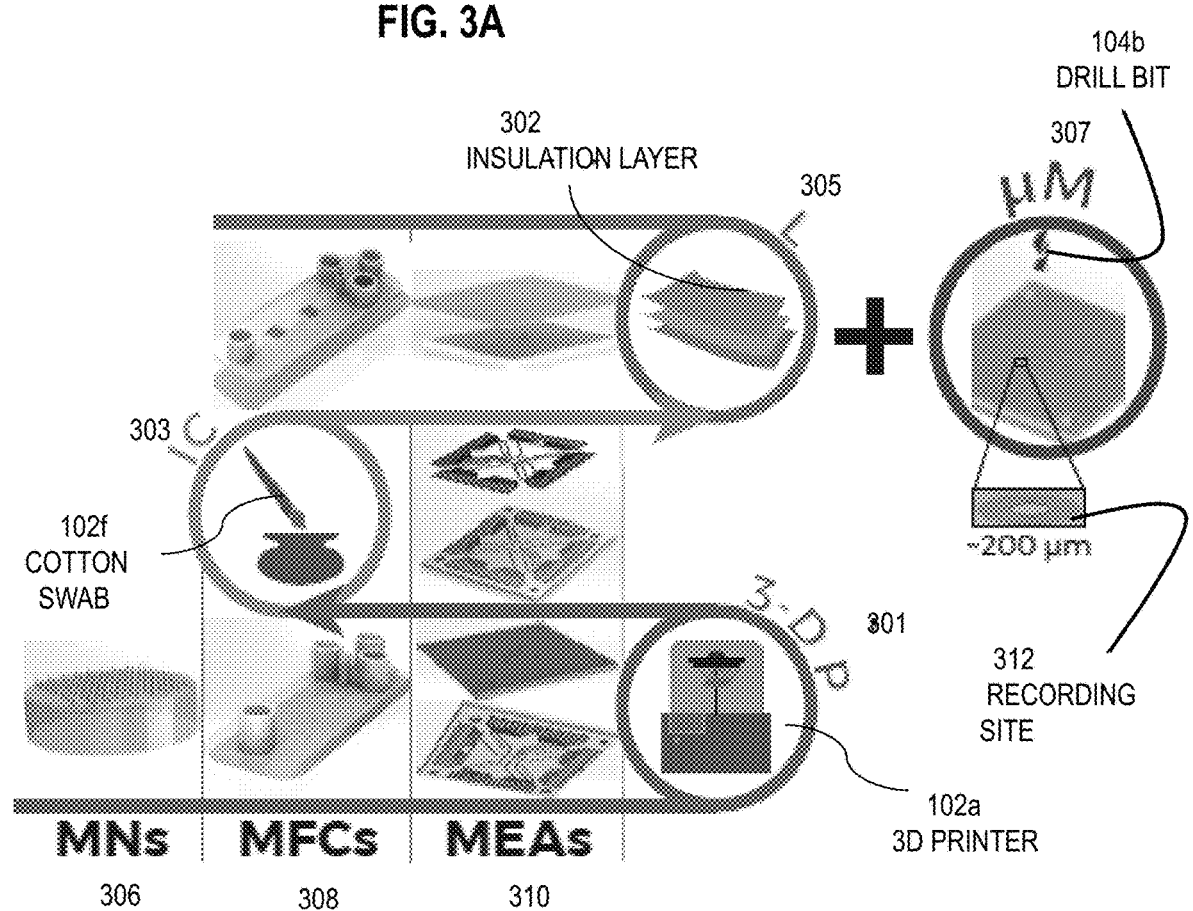
FIG. 3A is an image that illustrates an example of additive and subtractive devices of the system of FIG. 1A, according to an embodiment.
Figure 3B:
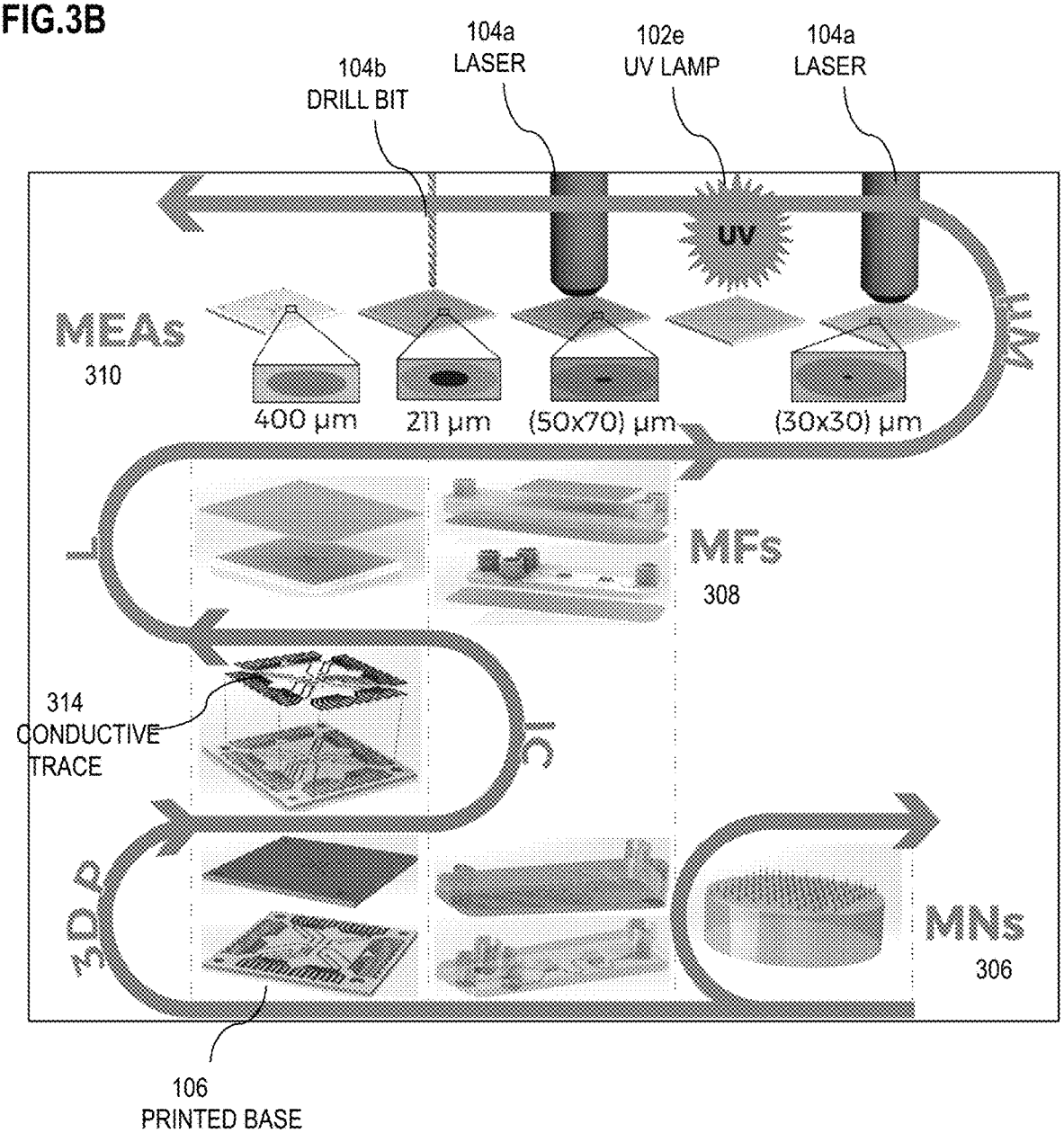

FIGS. 3A-3C are images that illustrate an example of additive and subtractive devices of the system 100 of FIG. 1A, according to an embodiment. In one embodiment, the method 200 is schematically depicted in FIGS. 3A-3C with steps in different combinations to fabricate the biological microdevices. In an embodiment, in step 201 the coarse scale additive process includes 3D printing 301 that is used to form the base of the object 106 after which additional coarse scale additive processes in subsequent steps 201 include ink casting additive process 303 to form the conductive layer on the base of the object 106 and lamination additive process 305 to form the insulation layer on the base of the object 106. Additionally, in step 208 the method 200 includes fine scale micromachining processes 307 to form one or more recording sites 312 in the object 106. Each of these additive and subtractive processes add various functionalities to the 3D printed device.

In some embodiments, the method 200 is hierarchical in nature with each additive or subtractive process building upon the functionalities provided by the earlier process. In an embodiment, the coarse scale ink casting additive process 303 can be used to define conductive tracks selectively on the object 106 and the coarse scale lamination additive process 305 may either act as packaging or insulating layers added to the object 106 and/or the selectively defined conductive tracks. In another embodiment, the fine scale micromachining subtractive processes 307 enables a synergy with the additive process steps. In one embodiment, subtractive definition of features is obtained with the micro-drill bit 104b or laser 104a micromachining based on the requirement of the final biological microdevice.

As depicted in FIG. 3C, in one embodiment forming of the microneedles (MN) 306 requires only the 3D printing additive process 301; the forming of the microfluidic (MF) channel 308 requires the 3D printing additive process 301 and the lamination additive process 305 and the forming of the MEAs 310 involves the 3D printing additive process 301, the ink casting additive process 303, the lamination additive process 305 and the micromachining subtractive process 307.

In some embodiments, in step 201 a design of each biological microdevice was developed using Solidworks® (Dassault Systems Inc., Waltham, Mass., USA) which allows generation of design concepts rapidly and offers unique tools for the creation, manipulation, and modification of designs using native and imported geometries. In an embodiment, in step 201 the designed stereolithography (SLA) file is printed using a Formlabs Form 2® printer 102a (Somerville, Mass., USA), where the laser 120 has a wavelength of about 405 nm and the printer 102a uses a photopolymer clear resin 125 (FLGPCL02). In an example embodiment, the X and Y-resolution of the laser beam 123 is determined by the spot size of the laser beam 123 which is about 140 µm. In another example embodiment, the axial resolution in Z direction of the laser beam 123 was kept at about 25 µm.

In some embodiments, the method 200 will now be discussed for forming the MEA 310. As depicted in FIG. 3B, a 3D design of the MEA 310 is targeted in the method 200. In an embodiment, the design of the MEA 310 has a unique non-planar design with a monolithic construction of the electrode tracks, electrode landing pads and vias both on the top and bottom faces of the MEAs 310. Such a non-planar design permits isolation of the electrode tracks from the top side of the MEA 310 thereby improving device reliability due to shorting or damages to the insulation layer. In one embodiment, the electrode design of the MEA 310 has a total of 9 working microelectrodes and 4 integrated reference ground electrodes and features a thickness of about 1 millimeter (mm). In one embodiment, the electrode vias are about 400 µm in diameter or in a range from about 100 µm to about 500 µm and the pitch between the electrodes is about 1 mm or in a range from about 400 µm to about 5 mm. In an embodiment, the diameter of the MEA 310 is about 30 µm or in a range from about 1 µm to about 150 µm. In yet another embodiment, the diameter of the MEA 310 is in a range from about 1 µm to about 500 µm. In an embodiment, this particular design of the microelectrodes is targeted at applications in precision plating of cells. In an embodiment, the width of the conducting traces is about 200 µm with a depth of about 100 µm. The electrode conducting traces terminate into contact pads which have a width of about 350 µm, a length of about 1 mm and a pitch of about 350 µm. In one embodiment, the contact pads are designed to interface with the Axion BioSystems® (Atlanta, Ga., USA) commercial MUSE® electronics and AxIS software35®.

In step 201, a first stage of the 3D printing 301 of the MEA 310 involves printing the base of the MEA 310 with the 3D printer 102a. In some embodiments, the angle 126 of the laser 123 in the 3D printer 102 is adjusted within a range from about 30 degrees to about 60 degrees. In an embodiment, the angle 126 is selected to be about 45 degrees. In another embodiment, to obtain an optimized print quality of the various features, the base of the MEA 310 is printed by the 3D printer 102a with the angle 126 set at each of 30°, 45°, 60° and 90° with respect to the surface of the resin 125. In another embodiment, a next stage of the 3D printing 301 of the base of the MEA 310 involves rinsing the printed base of the MEA 310 twice in isopropyl alcohol (Sigma-Aldrich, St. Louis, Mo., USA) for 10 minutes. In another embodiment, a next stage of the 3D printing 301 of the MEA 310 involves drying the base of the MEA 310 with the nitrogen gun 102g. In some embodiments, the base of the MEA 310 is not temperature cured using the heater 102d in order to avoid deformation of the MEA 310 base due to compressive thermal stress. In an embodiment, as the laser beam 123 is focused onto the surface of the liquid photopolymer to print each layer 127 of the base of the MEA 310, diffraction of the laser beam 123 limits the print resolution resulting in the electrical vias and the micro-troughs intended for ink casting of the conducting traces not being fully defined. FIGS. 4A-4D are images that illustrate an example of a base of the MEA 310 printed by the 3D printer 102a of FIG. 1A at different angles, according to an embodiment. FIG. 4A depicts a base of the MEA 402 that is printed using the 3D printers 102a with an angle 126 at about 0 degrees. In an embodiment, the MEA 402 of FIG. 4A depicts the lack of definition in the electrical vias and micro-troughs due to the diffraction of the laser beam 123 with the angle 126 of about 0 degrees.

In an embodiment, at an angle 126 of about 90 degrees, the cross-section of the base of the MEA 310 being printed is depicted in FIG. 5A, where the laser 123 prints only an arc of the electrical via of the MEA 310. In an embodiment, as the z-axis resolution is about 25 μm, the sagitta length of the arc would be about 8 μm as the radius of the MEA via is about 200 μm. In an embodiment, the sagitta length of the arc is therefore much smaller than the laser spot size and curing in undesired places of the photopolymer occurs and the arc of the via is not defined, as depicted in FIG. 5B. When the 3D printing 301 progresses the incomplete curing of a single layer propagates throughout the entire geometry of the vias resulting in a print failure. This failure is attributed to the fact that the diffraction effects are maximized as the laser light is completely perpendicular to the geometry being printed. In successive layers the diffracted light cures the photopolymer in undesired areas 512 around its spot size and when coupled with the misprinting of the first layer of the vias, the resultant print is a completely closed feature as depicted in FIG. 4A. This indicates that it would be judicious to print at the lowest angles 126 with respect to the surface of the resin 125 in order for the laser beam 123 to cure the entire via geometry defined in the polymer while it prints each layer. As the vias are resolved in the XY-axis (FIGS. 5C-5D), the diffraction effect will only alter the print dimensions in the XY-plane affecting the design dimensions of the vias and the micro-troughs resulting in print failure of vias less than 400 μm in diameter for a thickness of 1 mm.

In an embodiment, 3D printing 301 of the MEAs 310 were additionally performed at angles 126 of about 45°, 60° and 90°. In an example embodiment, the effect of diffraction leading to false printing is observed to significantly decrease when the angle 126 is increased to about 30° to print the base 404 of the MEA, as depicted in FIG. 4B. Although the electrical vias are open, the micro-troughs for the conducting traces are not well defined due to a reduced feature size (200 μm) as compared to the vias (400 μm). At an angle 126 of about 45°, the print quality is significantly improved with all the features being properly defined in the base 406 of the MEA as shown in FIG. 4C. At higher angles 126 including about 90 degrees, although the base of the MEA 310 is printed as per the design, debris was detected on the surface of the base 408 of the MEA as shown in FIG. 4D. The accumulation of the debris which can become a permanent feature on the printed surface can be attributed to the fact that the MEA base 408 is now being printed in a completely horizontal direction and the entire MEA base surface is making contact with the liquid photopolymer.

In step 203, it is determined that additional coarse scale additive processes are to be performed to form additional layers of the MEA 310 and thus the method 200 moves back to step 201 and the base of the MEA 310 is moved to the appropriate additive device 102 using the conveyor belt 108. In some embodiments, the additional coarse scale additive process is the ink casting 303 to define conductive traces on the base of the MEA 310. In one embodiment, in step 201 for the ink casting, conductive traces are defined on the base of the MEA 310 using Epo-tek® EJ2189 (Epoxy Technologies Inc., Billerica, Mass., USA), an electrically conductive (e.g. resistivity values range: 0.0005-0.009 Ohm-cm), silver filled epoxy paste suitable for low temperature curing from ambient to 80° C. In an embodiment, in step 201 the conductive ink is coated with the cotton swab 102f (e.g. Pur-Wraps®, Puritan Medical Products, Guilford, Me., USA) onto the entire base of the MEA 310 with the MEA geometry. In an embodiment, the paste is subsequently removed utilizing a different cotton swab from the device area which yet leaves the paste in the micro-troughs (e.g. residing at 100 μm below the surface) intended for the conductive traces and conductive vias due to the difference in height between the top and bottom levels of the paste. In another embodiment, in step 201 the coated base of the MEA 310 is cured using the heater 102d at about 40° C. for about 3 hours, is subsequently rinsed in isopropyl alcohol and is subsequently dried with the nitrogen gun 102g. In some embodiments, at this stage the formed object may be used as a MEA base with microelectrodes that have a diameter of about 400 μm due to its unique non-planar design.

In step 203, it is determined that additional coarse scale additive processes are to be performed to form additional layers of the MEA 310 and thus the method 200 moves back to step 201 and the base of the MEA 310 is moved to the appropriate additive device 102 using the conveyor belt 108. In some embodiments, the additional coarse scale additive process is the lamination 305 additive process to add an insulation layer on the base of the MEA 310. In an embodiment, to fabricate smaller microelectrodes, the lamination of an insulation layer is performed on the base of the MEA 310. In another embodiment, the lamination of the insulation is performed by casting/curing of an epoxy-based negative photoresist (e.g. SU-8) on electrode openings obtained by the fine-scale subtractive processes in step 208 discussed below such as micro-drilling with the drill bit 104 or laser micromachining with the laser 104a.

In an embodiment, in step 201 the laminating additive process 305 is performed by using an insulating layer (e.g.

Medco® RTS3851-17 adhesives ~50 μm thick plus Poly Ethylene Terephthalate (PET) ~20 μm thick; Medco Coated Products, Cleveland, Ohio, USA). In an embodiment, PET is biocompatible and has been used successfully as a substrate for MEAs 310. In an embodiment, in step 201 the liner on the adhesive layer is removed and subsequently the adhesive layer is affixed to the base of the MEA 310. In another embodiment, in step 201 the cutting device 102h (e.g. scissors) are used to cut the adhesive layer and define its final shape based on a shape of the base of the MEA 310. In another embodiment, in step 201 the base of the MEA 310 and the PET/adhesive layer are pressed with about 100 pounds of force at room temperature for about 30 seconds with a manually operated, benchtop hydraulic laminating press 102b (e.g. laminating press manufactured by Carver, Inc., Wabash, Ind., USA). In an example embodiment, a final thickness of the insulation layer including the adhesive and PET layer is approximately 63 μm after the pressing step. This lamination additive process is remarkably fast and simple.

In some embodiments, the additional coarse scale additive process is the lamination 305 additive process to add a thin insulation layer on the base of the MEA 310. For defining thinner insulation layers comparable with commercial MEA devices, SU-8-negative tone photo-epoxy (e.g. GM 1050 from Gersteltec, Pully, Switzerland) was used. In an embodiment, in step 201 after the photo-epoxy is adhered to the base of the MEA 310, the base is positioned in the spin coater 102c which is operated at about 1660 revolutions per minute (rpm) for about 40 seconds with a ramp of about 100 rpm after application of the photoresist. In another embodiment, in step 201 after the spin coating the base of the MEA 310 is positioned in the heater 102d and soft baked at about 40° C. for about 10 minutes, the base of the MEA 310 is subject to UV flood exposure with the UV lamp 102e (e.g. wavelength of 365 nm) to completely crosslink the SU-8 photoresist using a UVP Blak-Ray™ B-100A (Upland, Calif., USA) UV lamp for about 3 minutes. In some embodiments, a post exposure bake was performed by positioning the base of the MEA 310 in the heater 102d for about 40° C. for about 5 minutes.

In some embodiments, after the 3D printing additive process forms the base of the MEA 310, the ink casting additive process forms the conductive traces on the base of the MEA 310 and the lamination additive process forms the insulation layer on the base of the MEA 310, the method 200 passes to step 203 and concludes that no further additive processes are to be performed. The method 200 then proceeds to step 205 where it is determined that fine scale subtractive processes are to be performed, to define one or more recording sites on the insulation layer of the MEA 310. In step 207, the conveyor belt 108 moves the base of the MEA 310 from the additive device 102 to the appropriate subtractive device 104 to perform the fine scale subtractive process.

In some embodiments, in step 208 the fine scale subtractive process is a micromachining subtractive process performed with the laser 104a. For the fabrication of the microelectrode recording sites, defined on the laminated adhesive using the laser, a green laser 104a (e.g. 532 nm) with a spot size of about (70×50) μm was fired at an energy level of about 50 millijoules (mJ) at a repetition rate of about 50 Hz using a QuickLaze 50ST2® (Eolite Lasers, Portland, Oreg., USA). In an embodiment, the laser 104a spot was aligned atop the lamination areas on the microelectrodes prior to the deployment of the laser 104a. For the definition of the recording sites in the insulation (e.g. SU-8) layer, the green laser 104a was fired with a spot size of (30×30) μm with an energy of about 25 mJ at a repetition rate of about 50 Hz.

In some embodiments, in step 208 the fine scale subtractive process is a micromilling subtractive process performed with the drill bit 104b. In an embodiment, for the fabrication of the microelectrode recording sites, an approximate 211 μm thick drill bit 104b (e.g. T-Tech®, Peachtree Corners, Ga., USA) was spun at about 55000 rpm in a T-Tech J5 Quick Circuit Prototyping Systems®. In an embodiment, in step 208 the total drilling time was about 39 seconds considering a drilling speed of about 180 holes/minute and about 13 drilling sites in a single MEA 310. This lamination/ micromilling fine scale subtractive processes for definition of the recording sites is significantly shorter than a standard lithographic technique.

In some embodiments, in step 210 it is determined whether another subtractive process is to be performed. In one embodiment, it is determined that an additional subtractive process is to be performed to form one or more additional recording sites of the MEA 310. In an embodiment, the method 200 moves back to step 207 to perform the additional subtractive process, such as forming additional recording sites.

In some embodiments, after determining that no additional subtractive processes are to be performed in step 210, in step 211 it is determined whether another additive process is to be performed. In an embodiment, it is determined that an additional additive process is to be performed to form packaging of the MEA 310 including culture wells with caps. In an embodiment, the method 200 moves back to step 201 to form the packaging of the MEA 310, where the culture wells and caps of the MEA 310 are designed using utilizing Solidworks® and 3D printed using the Form Labs Form 2 printer 102a. In step 201, the fabricated MEAs 310 are then attached with the culture well using an epoxy (e.g. Epo-tek® 353ND) to form a packaged MEA. In an embodiment, in step 201 the epoxy was formed by mixing parts A and B of the epoxy in a ratio of about 10:1 (by weight) and applied to the underside of the culture well and the fabricated MEAs were assembled face down. In a further embodiment, the packaged device is placed in the heater 102d and cured at about 40° C. for about 4 hours. In a further embodiment, in step 201 the devices were tested for any leaks with ethanol and DI water prior to the electrical and electrochemical measurements.

In some embodiments, after forming the packaged MEA 310, the method 200 passes to step 203 where it is determined whether another additive process is to be performed. In one embodiment, it is determined that an additional additive process is to be performed to deposit microelectrode material at the recording sites of the MEA 310 fabricated in step 208. In step 204, the conveyor belt 108 moves the culture well and packaged MEA 310 to the transfer pipette 102i to perform the deposition of the microelectrode material. In some embodiments, the deposited material is micro/nanomaterials that impart specific functionality to the electrode. In one embodiment, the deposited material includes nanoporous Platinum, micro/nanoporous gold and PEDOT:PSS [poly (3,4-ethylenedioxythiophene]. For electroless deposition of the microelectrode material (e.g. porous platinum), a solution is prepared including 0.01 weight percentage (wt %) platinum using about 3.75 mL (~8% chloroplatinic acid from Sigma-Aldrich), 0.2 mL of 0.005 wt % lead acetate (Sigma-Aldrich®), 4.065 ml of 1.23 M HCl (Sigma-Aldrich®) and 2.085 ml of DI water. In an embodiment, in step 201 approximately 3 mL of this solution is transferred to the MEA culture well using the transfer pipette 102*i* and passive electroless plating was performed for about 1, 3 and 6 hours respectively to estimate the time required for obtaining complete platinum coverage on the electrodes. In an embodiment, optical observations of the electrolessly plated platinum were performed at the pre-defined time periods utilizing a microscope after the MEA device 310 was rinsed with DI water and the liquid was removed with nitrogen blow drying using the nitrogen gun 102*g*.

After the deposition of the microelectrode material, the method moves to steps 203, 205 where additional additive and subtractive processes are not to be performed, after which the method 200 ends. In an embodiment, one or more measurements of the formed MEA 310 are then performed to verify that the formed MEA 310 meets various performance standards. In an embodiment, impedance measurements of the MEAs 310 are performed using Bode 100® (Omicron Labs, Houston, Tex., USA) with Dulbecco's Phosphate Buffer Solution® (Thermo Fisher Scientific, Waltham, Mass., USA) as the electrolyte. In another embodiment, the impedance scans are carried out from 10 Hz to 1 MHz with a platinum wire (eDAQ®, Denistone East, Australia) as the counter electrode. In another embodiment, cyclic voltammetry (CV) was performed using Potentiostat 466® system (from eDAQ). In an example embodiment, the CV measurements are performed with a 3-electrode setup with a silver/silver chloride (Ag/AgCl) wire acting as the reference electrode and a Pt wire used as the counter electrode with Dulbecco's PBS® (1×) as the electrolyte. CV scans were performed from −1V to 1V with scan rates of 50 mV/s, 100 mV/s, 160 mV/s, 200 mV/s and 250 mV/s to estimate the capacitance of the electrodes. In another embodiment, optical imaging of the microelectrodes was performed using a BX51M® microscope (Olympus, Center Valley, Pa., USA). In an embodiment, scanning electron microscope (SEM) imaging and Energetic Dispersive X-ray Spectroscopy (EDS) analysis of the printed devices and the electroless deposited platinum (Pt). are performed using JSM 6480® (JEOL, Peabody, Mass., USA).

Figure 6A:
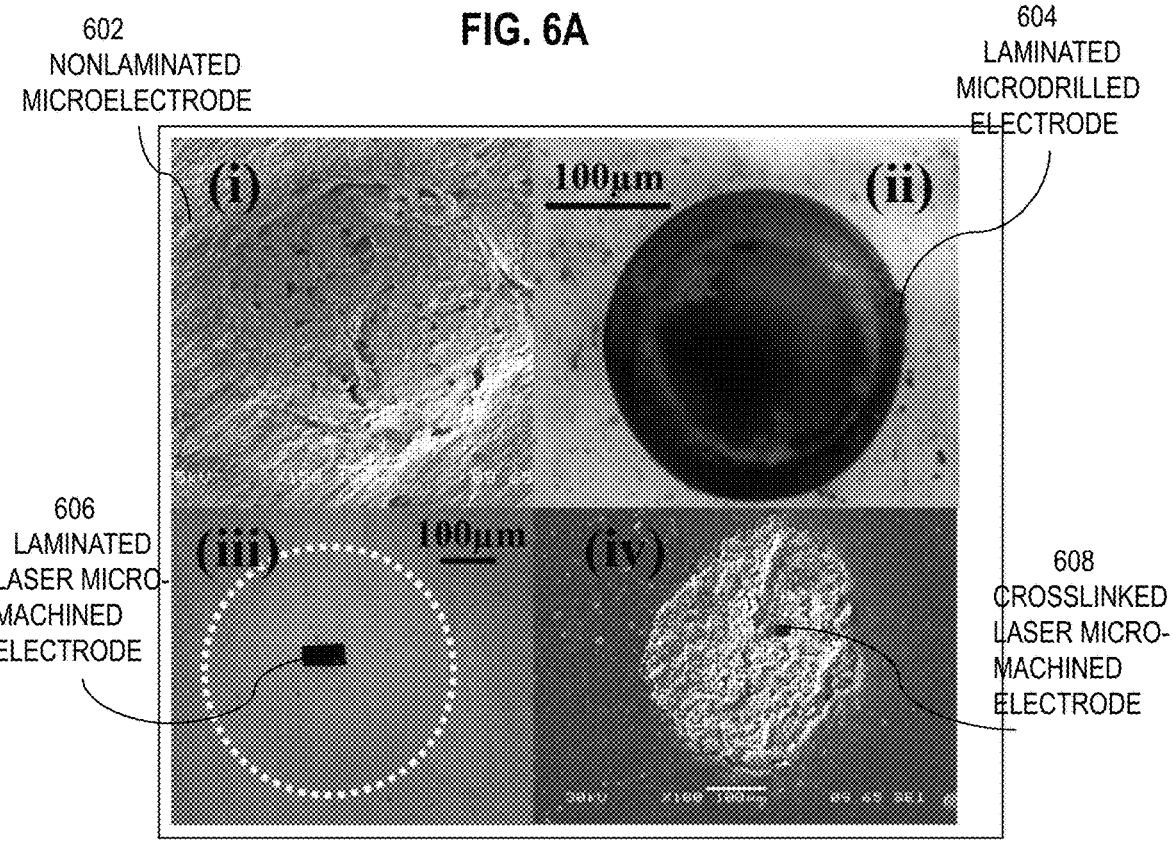
FIG. 6A is an image that illustrates an example of different types of microelectrodes formed using the system of FIG. 1A, according to an embodiment.
Figure 6B:
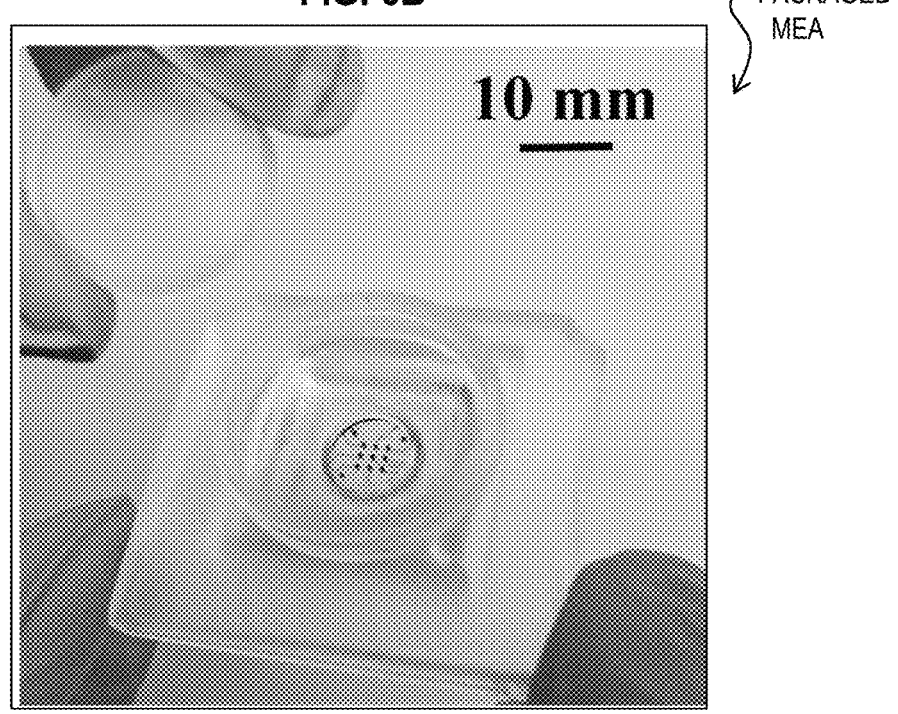
FIG. 6B is an image that illustrates an example of a packaged MEA formed using the system of FIG. 1A attached to a culture well, according to an embodiment.
Figure 9A:
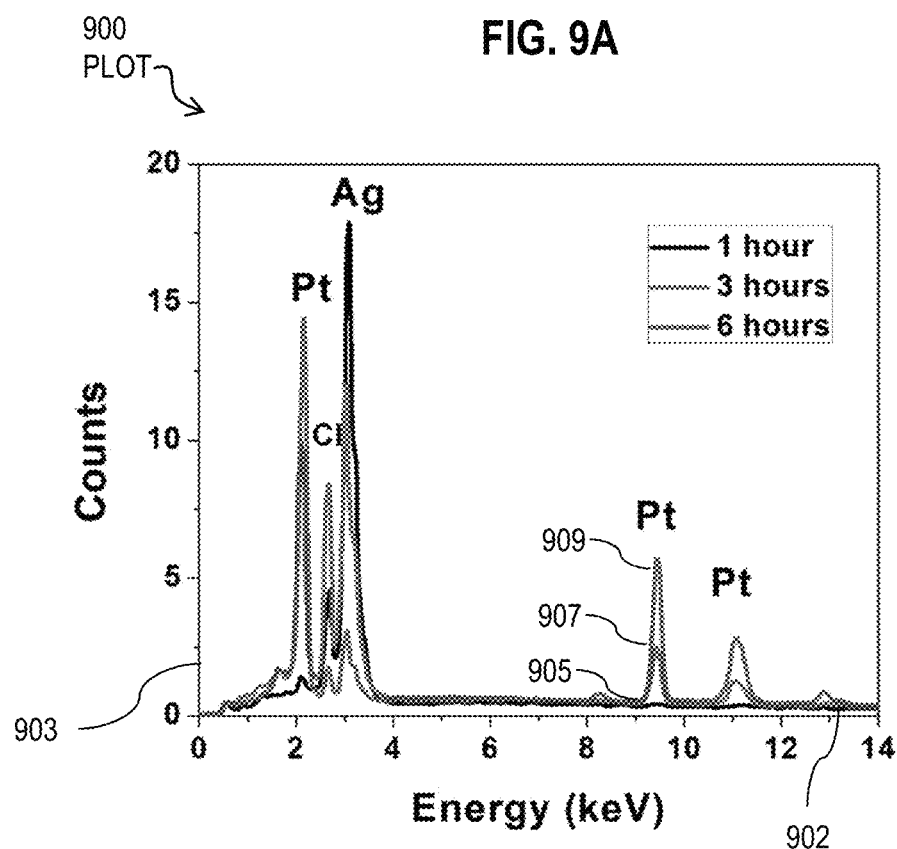
FIG. 9A is a plot that illustrates an example of platinum coverage on a surface of a functional MEA formed using the system of FIG. 1A at various stages of electroless plating, according to an embodiment.
Figure 9B:
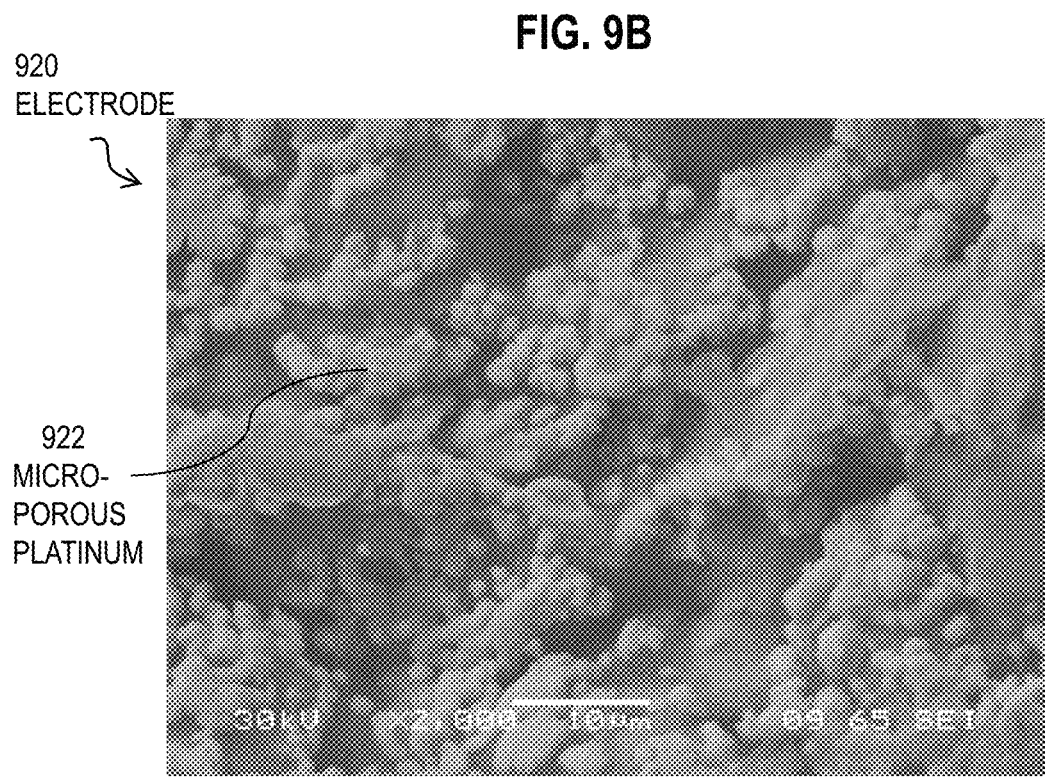
FIG. 9B is an image that illustrates an example of micro-porous platinum deposited on the electrodes of a functional MEA formed using the system of FIG. 1A, according to an embodiment.
Figures 13A, 13B, 13C, 13D, 13E, 13F:
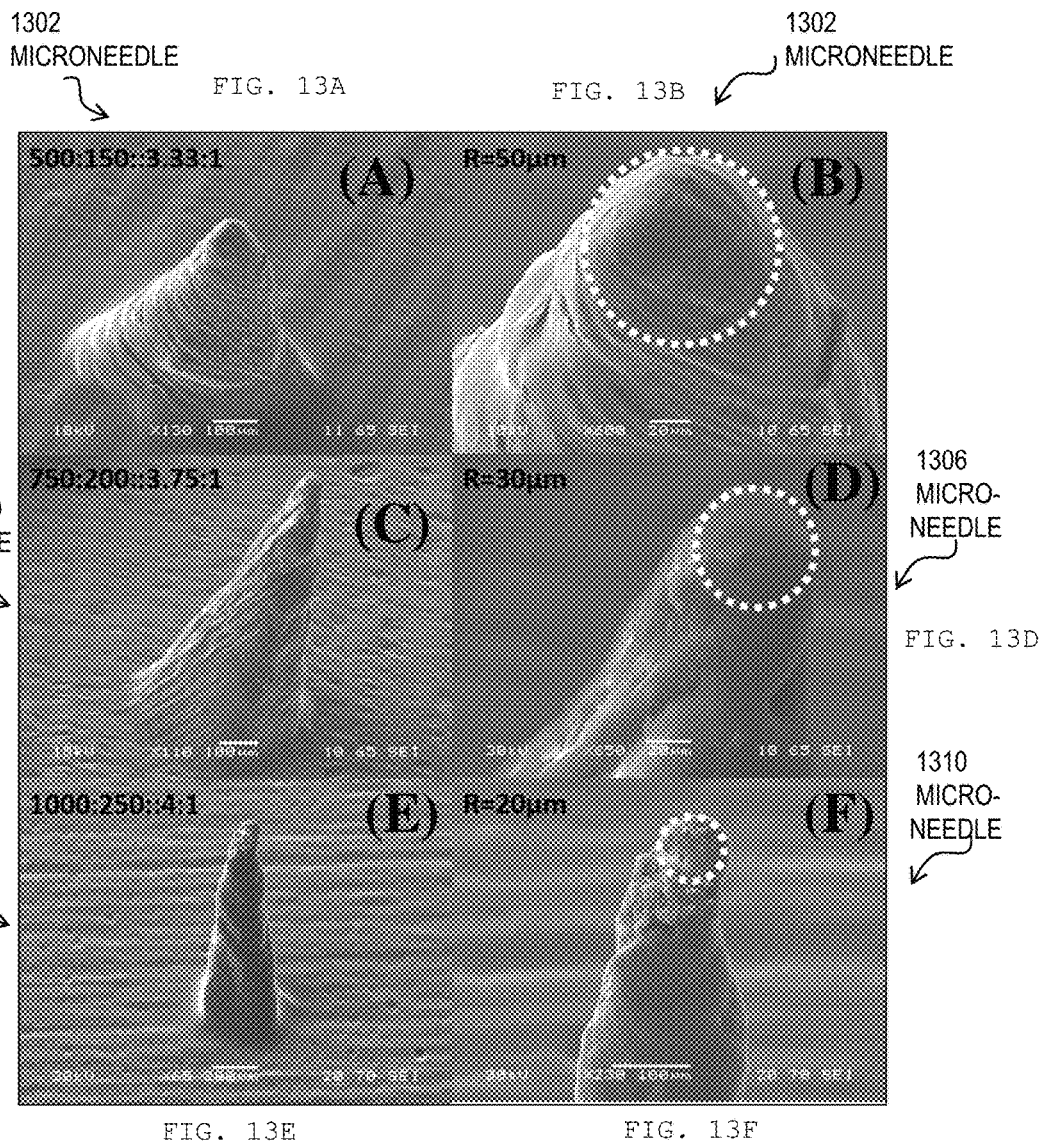
FIGS. 13A-13F are images that illustrate an example of a microneedle (MN) formed using the system of FIG. 1A with various aspect ratios, according to an embodiment.

In an embodiment, FIG. 6A depicts Scanning Electron Microscope (SEM) and optical micrographs of the (i) non-laminated microelectrode 602 (e.g. ~400 μm diameter), (ii) the adhesive laminated and micro-drilled electrode 604 (e.g. ~211 μm diameter), (iii) adhesive laminated and laser micromachined electrode 606 (e.g. 70×50 μm in size) and (iv) the SU-8 cast/crosslinked and laser micromachined electrode 608 (e.g. 30×30 μm in size) respectively. In an embodiment, microelectrodes comparable to standard commercial designs are created with the fine scale subtractive processes. FIG. 6B depicts an optical micrograph of a 3D printed MEA 310 after packaging and electroless plating. FIGS. 8A-8D show the effect of electroless platinum plating on the ink casted silver electrodes for different time periods, specifically with no plating (FIG. 8A), 1 hour (FIG. 8B), 3 hours (FIG. 8C) and 6 hours (FIG. 8D). In one embodiment, the electrodes depict a change in shading from gray to black with an increase in time. In order to validate the presence of platinum, SEM and EDS analysis of the electrodes were performed. In an embodiment, Energetic Dispersive X-ray Spectroscopy (EDS) analysis is depicted in FIG. 9A confirms the presence of platinum and the coverage on the surface is seen to increase from 7% wt. to 31% wt. and finally to almost 95% wt. after 1 hour, 3 hours and 6 hours of electroless deposition, respectively. The horizontal axis 902 is energy in units of kilo-electron volts (keV) and the vertical axis 903 is counts that is unitless. A first trace 905 depicts the level of platinum after 1 hour, the second trace 907 depicts the level of platinum after 3 hours and the third trace 909 depicts the level of platinum after 6 hours. FIG. 9B is an example of an SEM image of micro-porous platinum 922 deposited on the electrodes 920 after about 6 hours of electroless deposition.

Figure 7A:
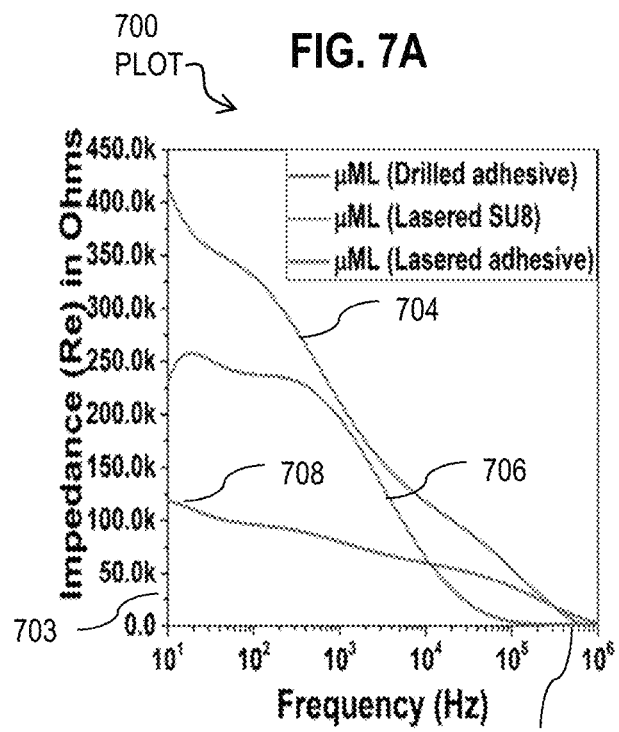
FIG. 7A is a plot that illustrates an example of average impedance of a formed MEA over a full frequency spectrum using the system of FIG. 1A, according to an embodiment.
Figure 7B:
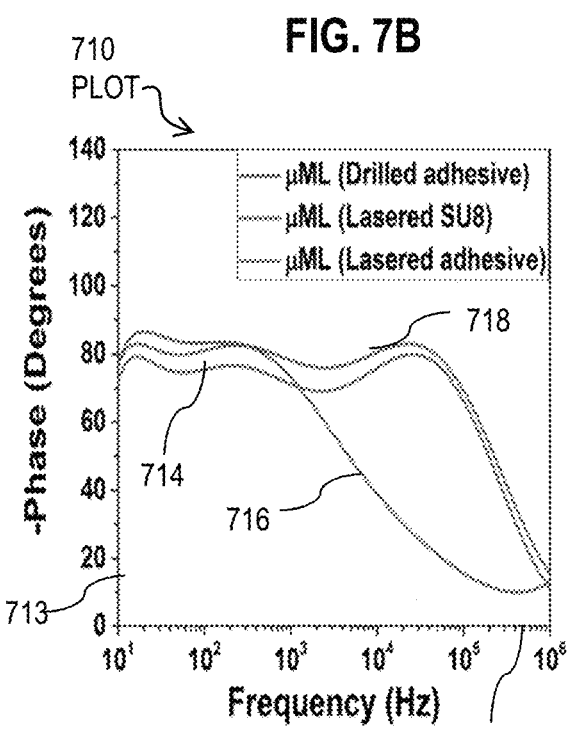
FIG. 7B is a plot that illustrates an example of phase response of a formed MEA using the system of FIG. 1A, according to an embodiment.

FIG. 7A is a plot 700 that illustrates an example of average impedance of a formed MEA 310 over a full frequency spectrum using the system 100 of FIG. 1A, according to an embodiment. FIG. 7B is a plot 710 that illustrates an example of phase response of a formed MEA 310 using the system 100 of FIG. 1A, according to an embodiment. The horizontal axis 702 is frequency in units of Hertz (Hz). The vertical axis 703 of FIG. 7A is impedance in units of Ohms (a). The vertical axis 713 of FIG. 7B is phase in units of degrees. In an embodiment, the plots 700, 710 depict the full spectrum impedance and phase response for the three distinct types of microelectrodes (e.g. average of N=9 of each electrode type) fabricated with the method 200. Trace 708 depicts the full spectrum impedance of the adhesive/polymer micro-drilled electrode, trace 706 depicts the full spectrum impedance of the SU-8 laser micromachined electrode and trace 708 depicts the full spectrum impedance of the adhesive/polymer laser micromachined electrode. Trace 718 depicts the phase response of the adhesive/polymer micro-drilled electrode, trace 716 depicts the phase response of the SU-8 laser micromachined electrode and trace 718 depicts the phase response of the adhesive/polymer laser micromachined electrode. It is observed that an average impedance of 80 kΩ, 190 kΩ and 194 kΩ is obtained at 1 kHz for the adhesive/polymer micro-drilled, adhesive laser micromachined and SU-8 laser micromachined electrodes respectively. FIG. 7C is a plot 740 that illustrates an example of average impedance of a formed MEA 310 over a full frequency spectrum using the system 100 of FIG. 1A, according to an embodiment. Trace 738 depicts the average impedance of the adhesive/polymer micro-drilled electrode, trace 736 depicts the average impedance of the SU-8 laser micromachined electrode and trace 738 depicts the average impedance of the adhesive/ polymer laser micromachined electrode. In an embodiment, FIG. 7C shows that the average impedance of the electrodes is reduced to 61 kΩ, 110 kΩ and 140 kΩ at 1 kHz after electroless platinum plating for 6 hours. In an embodiment, the average 1 kHz impedance of the formed MEA 310 is in a range from about 20 kΩ to about 200 kΩ. In an embodiment, these values are comparable to similar sized microelectrodes fabricated utilizing sophisticated and expensive cleanroom-based technologies. Impedance and phase characteristics of the non-laminated microelectrodes are presented in FIG. 10. FIG. 10 is a plot 1000 that illustrates an example of full spectrum impedance and phase of a formed MEA 310 using the system 100 of FIG. 1A, according to an embodiment. The horizontal axis 1002 is frequency in units of Hertz (Hz), the left vertical axis 1003 is impedance in units of Ohms (Ω) and the right vertical axis 1005 is phase in units of degrees. Trace 1008 depicts the full spectrum impedance of the adhesive/polymer micro-drilled electrode without electroless platinum, 1006 depicts the full spectrum impedance of the SU-8 laser micromachined electrode without electroless platinum and trace 1008 depicts the full spectrum impedance of the adhesive/polymer laser micromachined electrode with electroless platinum.

Figure 7D:
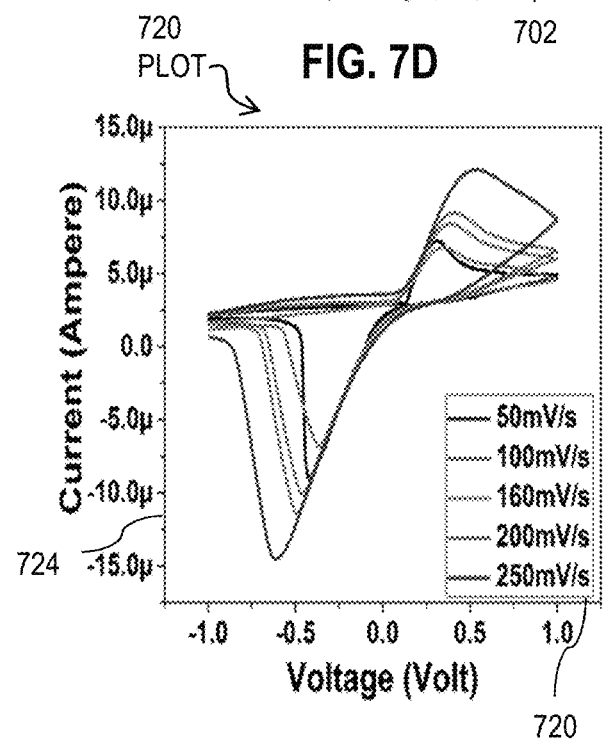
FIG. 7D is a plot that illustrates an example of cyclic voltammetry of a formed MEA using the system of FIG. 1A before electroless plating, according to an embodiment.
Figure 7E:
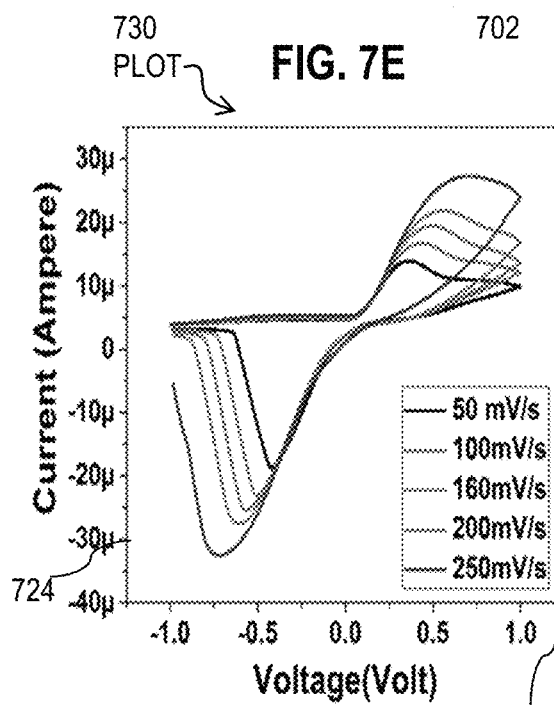
FIG. 7E is a plot that illustrates an example of cyclic voltammetry of a functional MEA using the system of FIG. 1A after electroless plating, according to an embodiment.

In some embodiments, cyclic voltammetry of the electrodes has additionally been performed for the smallest microelectrodes (e.g. 30×30 μm in size) that were developed using the method 200. In an embodiment, to estimate the change in the double-layer interfacial capacitance (Cdl) of the electrodes after electroless platinum deposition, scan-rate variation of the SU-8 devices were performed. FIG. 7D is a plot 720 that illustrates an example of cyclic voltammetry of a formed MEA 310 using the system 100 of FIG. 1A before electroless plating, according to an embodiment. FIG. 7E is a plot 730 that illustrates an example of cyclic voltammetry of a formed MEA 310 using the system 100 of FIG. 1A after electroless plating, according to an embodiment. The horizontal axis 720 is voltage in units of volts (V). The vertical axis 724 is current in units of amperes. FIG. 7F is a plot 750 that illustrates an example of a current-scan rate of a formed MEA 310 using the system 100 of FIG. 1A before and after electroless plating, according to an embodiment. The plot 750 depicts the current-scan rate 746 after plating and the current-scan rate 748 before plating. In an embodiment, the current/scan rate plot has a linear fit as expected and the capacitance values were extracted from the slope of the graphs. It is observed that the capacitance values doubled due to electroless plating from 1.5 µF to 3 µF. In an embodiment, this significant result advantageously demonstrates the potential for the method 200 to form microelectrodes for use in cardiac and neural electrophysiology.

In some embodiments, the method 200 will now be discussed for forming the MN 306. In an embodiment, in FIG. 3B an array of solid microneedles (MNs) 306 are formed using the method 200. In an embodiment, the microneedle MN 306 patch printed in step 201 by the 3D printer 102a has a diameter of about 25 mm and a thickness of about 5 mm with an array of 81 microneedles arranged in a 9×9 matrix. In another embodiment, microneedles 306 printed in step 201 have varying aspect ratios (e.g. ratio of needle height to needle diameter) including 3.33, 3.75 and 4. In one embodiment, the printed microneedles 306 in step 201 have an aspect ratio within a range from about 1 to about 10. In an example embodiment, these aspect ratios correspond to needle height/needle diameter ratios of about 500 µm/150 µm, 750 µm/200 µm and 1000 µm/250 µm that are designed and printed in step 201 with the 3D printer 102a. In an embodiment, the base of the MN 306 was printed using the 3D printer 102 where the angle 126 is selected within a range from about 30 degrees to about 60 degrees. In an example embodiment, the angle 126 is set to about 45 degrees. In another embodiment, to evaluate the accuracy of the angular optimization, a test MN geometry (e.g. 1000 µm base diameter, 1000 µm height) was printed by the 3D printer 102a at angles 126 of about 0°, 45°, 60° and 90° with respect to the surface of the resin 125. In some embodiments, in step 201 after printing the MN 306 array with the printer 102a, the MN 306 array is positioned in the heater 102d and subsequently cured at a temperature of about 60° C. or a temperature in a range from about 40° C. to about 70° C. and for about 60 minutes or a time in a range from about 40 minutes to about 80 minutes to obtain a high tensile strength (65 MPa).

In an embodiment, the effect of temperature curing of the microneedles 306 that affects the mechanical properties of the MNs is shown in FIGS. 11A and 11B. In the absence of temperature curing the microneedle tip of an optimized geometry is observed to bend with a force of approximately 10 N/patch, as shown in FIG. 11A. This force translates to approximately 50 MPa per tip which is greater than the Ultimate Tensile Strength (UTS) of human skin. However, after the microneedles are cured (e.g. curing cycle of 60° C. for 60 minutes), their tips remain intact when subject to a similar puncturing force (10 N/patch), as depicted in FIG. 11B.

In an embodiment, a test mironeedle geometry (e.g. 1000 µm base diameter, 1000 µm height) was printed using the 3D printer 102a at similar angles 126 (e.g. 0°, 45°, 60°, 90°) as the MEAs 310. The printed MNs 412, 414, 416, 418 are depicted in FIGS. 4E-4H. In an embodiment, it is observed that the lagging face of the microneedle geometry is severely misprinted for 90°, as depicted in FIG. 4E, because as one half of the needle 412 is printed, it offers the greatest surface area at the liquid photopolymer interface and the printing would actually be similar to the printing results at 0°. In an embodiment, at an angle 126 of 0° with respect to the horizontal, as the microneedle printing starts with the maximum surface area (as opposed to 90° where it starts with the minimum surface) the entire microneedle 418 surface is damaged thereby giving it the characteristic feature of a 'burning candle' as evident from FIG. 4H. The surface damages are observed to reduce at the angle 126 of about 60° as shown in FIG. 4G with a resultant optimum print angle 126 at 45° as shown in FIG. 4F. Based on these observations, in one embodiment, ~45° is an optimum print angle 126 for the 3D printer 102a when printing the designs of biological microdevices. In another embodiment, a range of the angle 126 from about 30 degrees to about 60 degrees is an optimum range of the print angle 126.

In some embodiments, after printing the base of the MN 306 in step 201 of the method 200, the method 200 moves to step 203 where it is determined that additional additive processes are not to be performed next. In some embodiments, the method 200 then moves to step 205 where it is determined that a subtractive process is to be performed. In an embodiment, the subtractive process is vapor polishing of the MN 306 performed by the glass beaker 104c. In an embodiment, in step 207 the base of the MN 306 is moved to the glass beaker 104c and in step 208 the base of the MN 306 is vapor polished using the acetone vapor filled glass beaker 104c. In one embodiment, in step 208 the fabricated MN 306 array is placed on top of an aluminum foil and placed inside the 1-liter glass beaker 102h. In another embodiment, Kimwipes® (Kimtech, Roswell, Ga., USA) were soaked in acetone and hung from the interior edges of the beaker 104c. The beaker 104c was sealed with Parafilm®, (Sigma-Aldrich) and the microneedles 306 were polished in acetone vapor for varying times (e.g. 4, 6 and 10 minutes) to obtain optimized polishing times. In some embodiments, inherent striations were additionally observed in the microneedles which is a result of the axial resolution being limited to about 25 µm. In an embodiment, the vapor polishing of the microneedles was performed in order to smoothen the surface of the microneedles as well as to sharpen the microneedle tips. FIGS. 12A-12D are images that illustrate an example of a microneedle (MN) formed using the system of FIG. 1A with various stages of acetone vapor polishing, according to an embodiment. In an embodiment, FIGS. 12A-12D depicts the effect of acetone vapor polishing of the 3D printed microneedles 306 at an angle 126 of about 45°. In an embodiment, the acetone vapor 'melts' the photopolymer during the subtractive process thereby making the surface of the microneedle 306 smooth while retaining the tip sharpness. However, it was observed that the exposure time to acetone vapor is significant and in one embodiment, the exposure time is limited (e.g. about 4 minutes was observed to be the optimum process time for the MN design) to obtain optimum polishing as depicted in FIG. 12B. In other embodiments, FIGS. 12C and 12D depict that the MN 306 after being severely affected for acetone vapor exposures of 6 minutes and 10 minutes respectively.

In some embodiments, after performing the vapor polishing subtractive process in step 208, the method proceeds to step 210 where it is determined that additional subtractive processes are not to be performed and the method 200 proceeds to step 211. In an embodiment, in step 211 it is further determined that additional additive processes are not to be performed and the method finishes and the MN 306 array is formed.

In an embodiment, since the MN 306 array is mainly intended for transdermal drug delivery by self-administration it is important that the MN 306 array punctures the top layer of skin, the stratum corneum. The puncturing force of the MN 306 array has to be carefully tailored since a smaller force would lead to unsuccessful skin penetration while larger forces could result in pain. The MN array 306 optimization (e.g. tip diameter and number of tips) has therefore been carried out in order to optimize a force that can make successful skin penetration with minimal discomfort to an individual. In an embodiment, to estimate this optimum value, measurements of applied force were performed using a circular Force-Sensitive Resistor (FSR, Adafruit, New York City, N.Y., USA) with the help of volunteers. The volunteers were requested to press upon the FSR with the following qualitative metrics: mild, gentle, hard and very hard. The resistance value of the FSR was recorded with the help of a multi-meter and converted to corresponding values of the force applied with the help of calibration graphs provided by the manufacturer.

In an embodiment, microneedle puncture tests were performed on a Human Skin Suture Training Model (Anatomicals IV Therapy Products, Lake Forest, Ill., USA) having a removable epidermis layer (Remedy Simulation Group, Perkasie, Pa., USA) for measurements of microneedle penetration depth and calculation of the optimum force required for uniform microneedle penetration. The applied force was measured using a calibrated FSR below the thumb of an individual pressing the microneedle array. Staining of the epidermis layer was performed using 1% wt. Rhodamine 6G (Sigma Aldrich) in water. Digital force gauge (Zhiqu Precision Instruments, China DS2 series; 10 N and 50 N) was used to calibrate the FSR and additionally was used to obtain microneedle fracture data. For the calibration experiment, the FSR/MNs was pressed with known values of force from the digital force gauge and the corresponding resistance value was recorded and converted to a force value as explained above. For the fracture data experiments, the Human Skin Suture Training Model was placed on one of the platens of the digital force gauge and the MN array was affixed with double sided adhesive tape on the other platen. The platens were pressed together at known values of force to fracture MNs and record the value. The MN fracture was observed optically with a microscope and confirmed with SEM measurements.

FIGS. 13A-13F are images that illustrate an example of a microneedle (MN) formed using the system 100 of FIG. 1A with various aspect ratios, according to an embodiment. SEM micrographs in FIGS. 13A-13F depict the effect of aspect ratio of the 3D printed needles 306. In an embodiment, for the MN 1302 with the aspect ratio of 3.33 (FIG. 13A), a radius of curvature of 50 µm (FIG. 13B) is observed. In another embodiment, for the MN 1306 with the aspect ratio of 3.75, a radius of curvature of 30 µm (FIG. 13D) is observed. In another embodiment, for the MN 1310 with the aspect ratio of 4, a radius of curvature of 20 µm is observed. In other embodiments, the MN formed using the system 100 has a radius of curvature within a range from about 5 µm to about 100 µm. In yet other embodiments, the MN formed using the system 100 has an aspect ratio within a range from about 1 to about 10.

FIG. 16 is a plot 1600 that illustrates an example of a qualitative assessment of multiple puncture forces imposed on a plurality of individuals. The horizontal axis 1602 is the number of each volunteer in the experiment and the vertical axis 1603 is force in units of Newton (N). In an embodiment, the force application experiments performed by 10 volunteers indicates that a force of approximately 10 N corresponds to a gentle push onto the skin surface is suitable for transdermal drug delivery by self-administration. In an embodiment, this force value was used to calculate the pressure on the tip of every microneedle 306 in the array. In an example embodiment, values of ~100 MPa, ~50 MPa and ~15 MPa are obtained for radius of curvature of 20 µm, 30 µm and 50 µm respectively for the microneedle patch having 81 individual microneedles. In another example embodiment, the chance of fracture increases with a smaller needle tip, however a larger MN tip may not be sufficiently strong to penetrate the stratum corneum of skin as UTS (Ultimate Tensile Strength) of skin is ~40 MPa. In an embodiment, mechanical analysis and puncturing experiments have therefore been carried out with microneedles having a radius of curvature of 30 µm printed in a 9×9 array which are well suited for the end application.

FIGS. 14A-14C are images that illustrate an example of puncture characteristics of an individual microneedle (MN) along the skin using different forces, according to an embodiment. In an embodiment, FIGS. 14A-14C show the individual microneedle puncture characteristics 1402, 1404, 1406 at different forces of 0.5 N, 10 N and 30 N respectively. FIGS. 14D-14F are images that illustrate an example of puncture characteristics of a microneedle (MN) array along the skin using different forces, according to an embodiment. In an embodiment, FIGS. 14D-14F show the MN array penetration characteristics 1408, 1410, 1412 at different forces of 0.5 N, 10 N and 30 N respectively. In an example embodiment, for very low forces (0.5 N) only some of the microneedles penetrate the artificial skin sample as evident with the R6G staining experiments as depicted in FIG. 14D. In another embodiment, an image of an individual puncture site 1402 in FIG. 14A additionally depicts that the MN was able to barely puncture the skin. For forces in the range of 10 N, the puncture site on the skin has a clear opening corresponding to a dimension of approximately 80 µm as depicted in FIG. 14B. Moreover, an ordered array with the MN dimensions and pitch is obtained after the staining experiment as depicted in FIG. 14E. In an embodiment, the distortion in the array is attributed to the curvature of the human skin suture model. For forces in the range of 30 N, the application of the force became non-uniform as the MN patch was being pressed too hard onto the skin surface. This resulted in puncture sites having large openings as depicted in FIG. 14C and partial needle array penetration as depicted in FIG. 14F.

FIG. 15A is an image illustrates an example of a MN formed using the system of FIG. 1A with a broken tip 1502 observed with an imposed force, according to an embodiment. FIG. 15B is an image illustrates an example of a MN formed using the system of FIG. 1A with complete breakage 1504 observed with an imposed force, according to an embodiment. In an embodiment, mechanical failure testing was performed with higher values of force to obtain the fracture strength of the microneedles. Breakage of the tip was observed from forces of ~30 N and a complete failure was obtained at values of ~40 N as shown in FIGS.

15A-15B, respectively. In an embodiment, the mechanical failure of the microneedles is therefore observed at a significantly higher amount of force (4×) than the force required for its successful operation in transdermal drug delivery.

In some embodiments, the method 200 will now be discussed for forming the MF device 308. In an embodiment, FIG. 3B shows a Y-channel microfluidic design realized using the 3D printing additive process 301 and lamination additive processes 305. In an embodiment, in step 201 the microfluidic channel is printed as an open channel on the bottom of the device using the 3D printer 102a during the 3D printing additive process 301. The printed microfluidic channel formed by the 3D printer 102a is subsequently sealed with a transparent adhesive lamination process and during the lamination additive process a closed microfluidic channel is defined. In an embodiment, such an approach results in achieving channel dimensions down to about 150 µm in width or a width in a range from about 50 µm to about 200 µm. In another embodiment, the MF device 308 has a depth of about 100 µm or in a range from about 50 µm to about 200 µm. In an example embodiment, the two entry and one exit ports allow for dispensing and collecting the fluids respectively. Two view-ports are additionally 3D printed by the 3D printer 102a during step 201 to observe the microchannel, one for viewing the Y-junction (View-Port 1) and the second for monitoring the micromixing process away from the Y-junction (View-Port 2). Further, in some embodiments, the coarse scale additive 3D printing process 301 can be extended for double-sided devices with features on both sides of a 3D printed base. Such multi-layer processing can result in sealed channels on both sides of a single substrate interconnected with 3D printed microfluidic vias of 400 µm width. In another embodiment, the vias of the 3D printed microfluidic devices have a diameter in a range from about 100 µm to about 500 µm.

In step 203, it is determined that additional coarse scale additive processes are to be performed to form the MF device 308 and thus the method 200 moves back to step 201 and the base of the MF device 308 is moved to the appropriate additive device 102 using the conveyor belt 108. In some embodiments, the additional coarse scale additive process is the lamination 305 additive process to add an insulation layer to the MF device 308 in a similar manner as discussed above with respect to the MEA 310. In an example embodiment, the lamination 305 additive process is performed on the MF device 308 using a specific adhesive lined with a polymer film, Medco®RTS3851-17.

In an embodiment, after forming the MF device 308, various measurements of the MF device 308 are performed. In an example embodiment, Gentian Violet® (Humco Austin, Tex., USA) and 1% wt. Rhodamine 6G° (Sigma Aldrich) are used as color markers to demonstrate fluid flow and mixing in the microfluidic channels. In another example embodiment, Gentian violet and Rhodamine 6G were dispensed into the two entry ports using a graduated pipette. In an embodiment, different concentrations of the PBS buffer solution were prepared by diluting the 1× concentration with Ethanol (Sigma-Aldrich) to obtain dilutions of 0.75×, 0.5×, 0.25× and 0.1× and utilized in the fluidic impedance measurements. Polystyrene (PS) latex beads (1.1 µm diameter, Sigma Aldrich) were used as a cell-like material for the optical analysis of the microfluidic mixer and the control (PS petri dish) with different concentrations in DI water (1×, 0.5×, 0.25× and 0.125×) prepared for the imaging experiments.

In another embodiment, after forming the MF device 308, various imaging steps are performed of the MF device 308. In an embodiment, the Y-channel junction was observed through View-Port 1 in the device 308. In an example embodiment, images of the Y-channel depicting micromixing were obtained using a transmitted light microscope (e.g. Olympus CK2) for qualitative analysis of the microfluidic design. For estimating the number of latex beads in the microfluidic channels, images were obtained in a dark field mode utilizing View-Port 2 of the device. A similar imaging technique was followed for estimating the number of beads in the control device (e.g. PS petri dish).

Figure 17A:
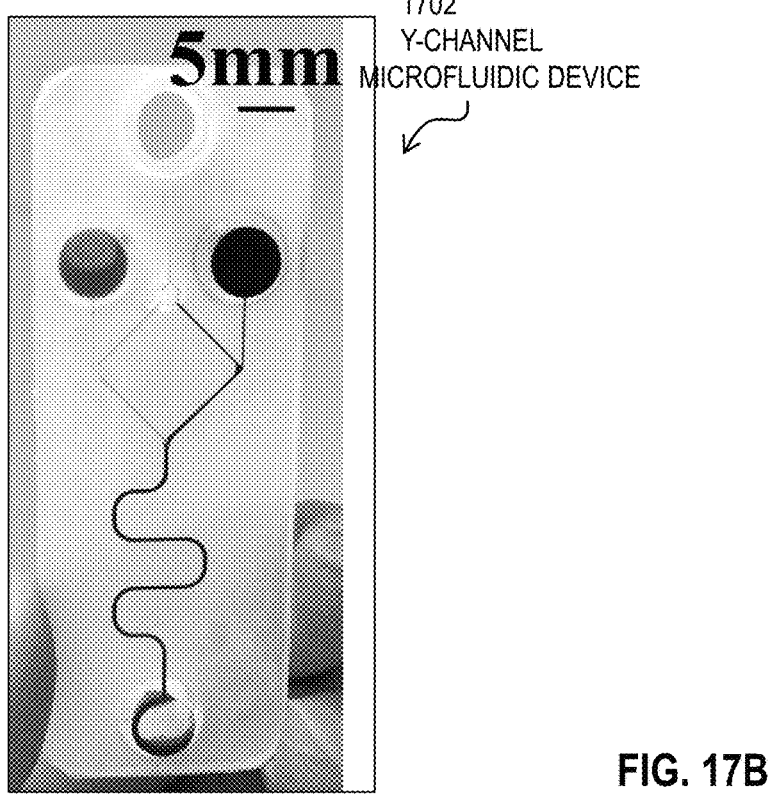
FIG. 17A is an image that illustrates an example of a Y-channel microfluidic (MF) device formed using the system of FIG. 1A, according to an embodiment.
Figure 17B:
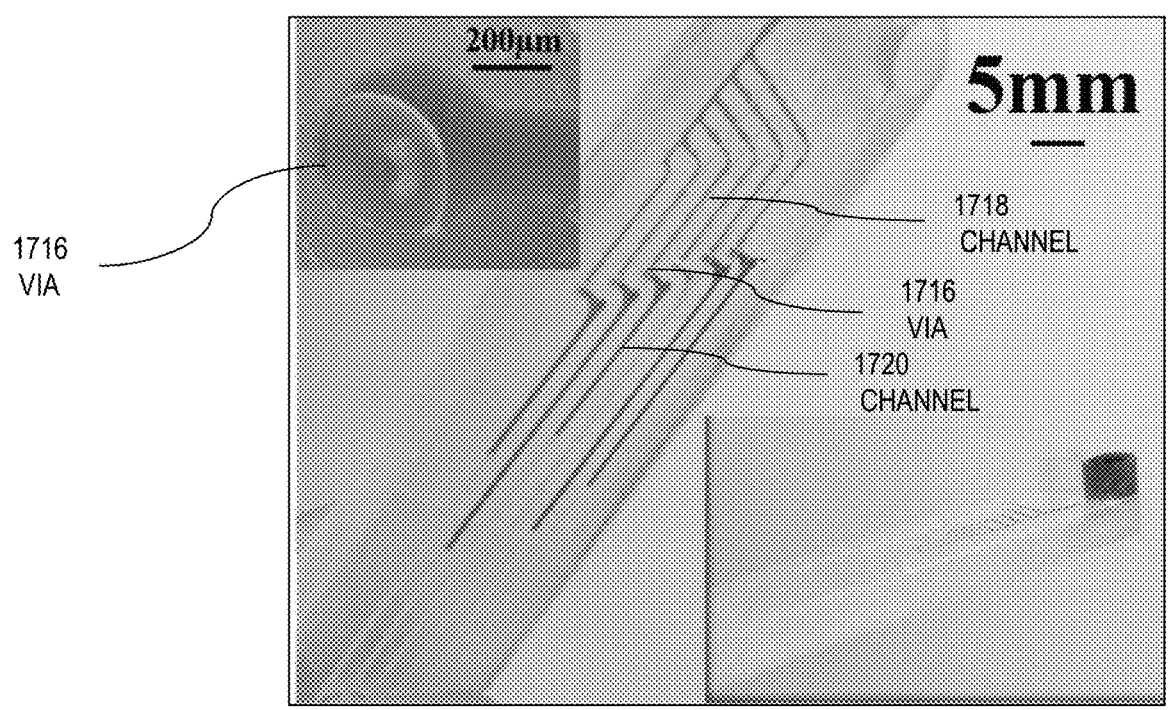
FIG. 17B is an image that illustrates an example of a microfluidic (MF) device formed using the system of FIG. 1A, according to an embodiment.

For the microfluidic devices, the adhesive lamination seals the microfluidic channel from the bottom making it possible to define channel dimensions 150 µm wide and 100 µm deep. In an embodiment, an opening of 150 µm was successfully defined with the 3D printer 102a as the channel was only 100 µm deep, which corresponds to only 4 printed layers. In other embodiments, other factors, such as microscopic contaminants of a cured resin additionally limits the accuracy of the final print. FIG. 17A is an image that illustrates an example of a Y-channel microfluidic (MF) device 1702 formed using the system 100 of FIG. 1A, according to an embodiment. FIG. 17B is an image that illustrates an example of a microfluidic (MF) device 1714 formed using the system 100 of FIG. 1A, according to an embodiment. In an embodiment, FIGS. 17A and 17B depict optical micrographs of a monolithically printed microfluidic channel from the top and the bottom after the introduction of flow with Gentian violet and R6G. In an embodiment, for the Y-channel MF device 1702 of FIG. 17A, it is seen that the violet and pink colors respectively of the reagents provides an evidence of mixing, although once the reagents are mixed, the color of the gentian violet begins to dominate the resulting fluid. In an embodiment, the functioning of a multi-layer printed microfluidic channel is depicted in FIG. 17B. In an example embodiment, it is observed that the liquid makes an easy transition from a channel 1718 in the top layer to a channel 1720 in the bottom microfluidic layers through the microfluidic via 1716 with a diameter of about 400 µm. In an embodiment, an optical micrograph of the microfluidic via 1716 and the fluid flowing through the via 1716 from the top to the bottom layers of the device are additionally shown in the inset.

Figure 18A:
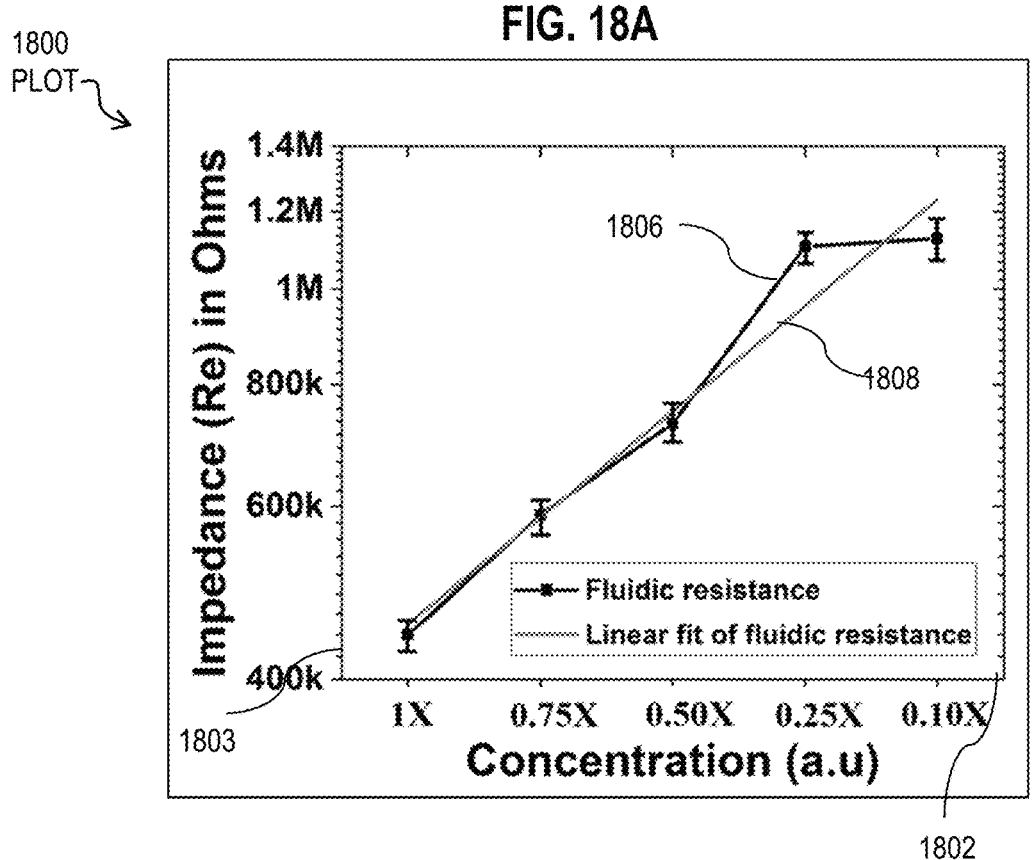
FIG. 18A is a plot that illustrates an example of fluidic resistance in the Y-channel of FIG. 17A for varying concentrations of fluid, according to an embodiment.

FIG. 18A is a plot 1800 that illustrates an example of fluidic resistance in the Y-channel 1702 of FIG. 17A for varying concentrations of fluid, according to an embodiment. The horizontal axis 1802 is concentration in arbitrary units (A.U.). The vertical axis 1803 is impedance in units of Ohm (a). The plot 1800 includes a trace 1806 of the fluidic resistance as well as a linear fit 1808 of the fluidic resistance for varying concentration of fluid. In an embodiment, to analyze the behavior of the printed microchannels, fluidic resistance in the Y-channel was obtained by varying the concentration of Dulbecco's PBS buffer. The linear fit 1808 of the fluidic resistance with concentration is obtained for similar volumes of injected solution (N=3) in the microfluidic device depicting an ohmic nature as expected.

Figure 18B:
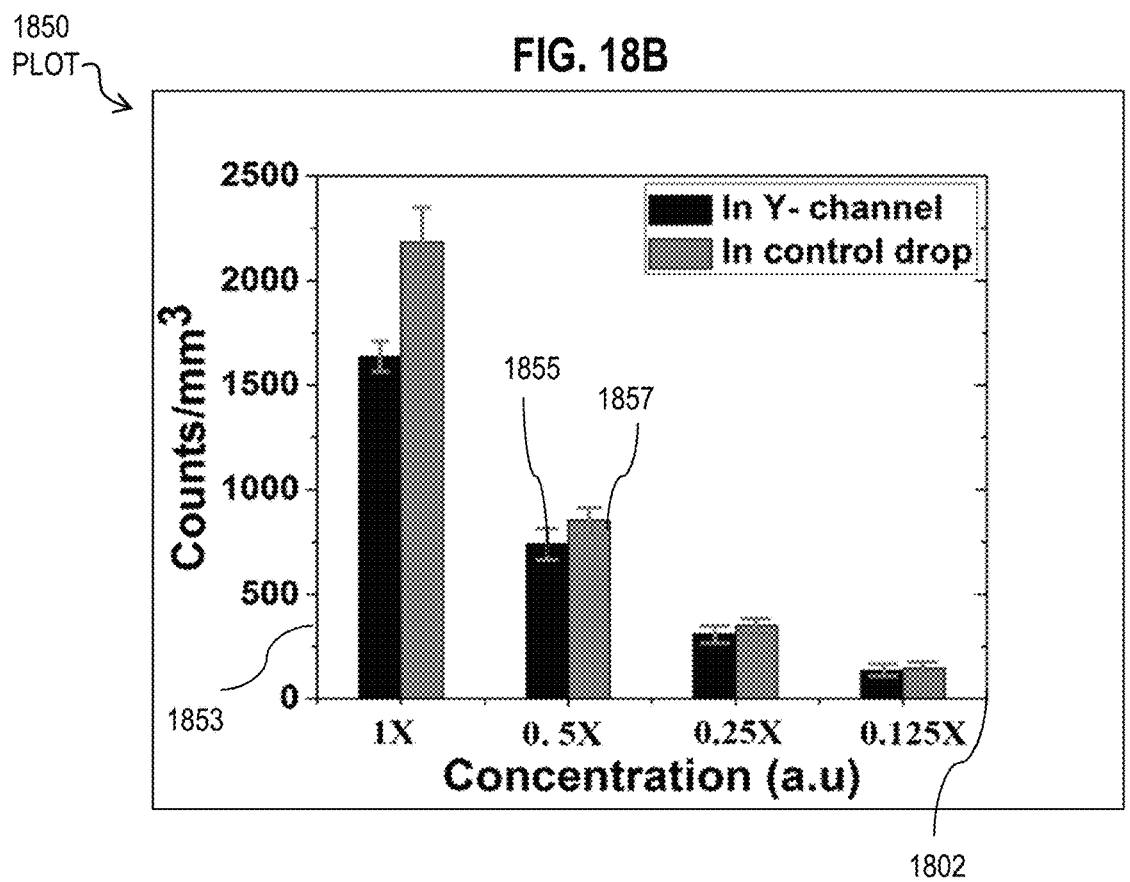
FIG. 18B is a plot that illustrates an example of optical count of beads in the junction of the Y-channel of FIG. 17A for different concentrations of fluid, according to an embodiment.

FIG. 18B is a plot 1850 that illustrates an example of optical count of beads in the junction of the Y-channel 1702 of FIG. 17A for different concentrations of fluid, according to an embodiment. The vertical axis 1853 is number of counts per unit volume in units of counts per cubic millimeter. The number of counts 1855 was counted in the Y-channel 1702 for different concentrations of fluid as well as the number of counts 1857 of a control drop in a petri dish. To further study the micromixing capability of the Y-channel 1702 in the presence of cell like material (~1.1 um PS beads), optical counting of the beads was performed for different concentrations of the PS beads in the junction of the Y-channel 1702 and compared to a polystyrene petri dish which is a gold standard in cell counting and optical imaging assays. In an embodiment, the measured values (N=3) in the junction of the channel are similar to that of a control drop of beads measured in the petri dish. In an example embodiment, for the lower end of concentration (0.125×) the tolerance of the difference is approximately 8%. In an example embodiment, for the upper end of the concentration (1×), there was observed agglomeration of the PS beads during the flow experiment in the channel which leads to higher values (~35%) of difference with the control and possibilities for counting errors. Nonetheless, a linear decrease in the particle counts is obtained for the varying concentrations of the PS beads in the microchannel with similar results in a PS petri dish demonstrating the ability of our 3D PICLμM devices to perform important microfluidic functionalities in optical assays and cell counting in biological applications.

3. COMPUTATIONAL HARDWARE OVERVIEW

FIG. 19 is a block diagram that illustrates a computer system 1900 upon which an embodiment of the invention may be implemented. Computer system 1900 includes a communication mechanism such as a bus 1910 for passing information between other internal and external components of the computer system 1900. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1900, or a portion thereof, constitutes a means for performing one or more steps of one or more methods described herein.

A sequence of binary digits constitutes digital data that is used to represent a number or code for a character. A bus 1910 includes many parallel conductors of information so that information is transferred quickly among devices coupled to the bus 1910. One or more processors 1902 for processing information are coupled with the bus 1910. A processor 1902 performs a set of operations on information. The set of operations include bringing information in from the bus 1910 and placing information on the bus 1910. The set of operations also typically include comparing two or more units of information, shifting positions of units of information, and combining two or more units of information, such as by addition or multiplication. A sequence of operations to be executed by the processor 1902 constitutes computer instructions.

Computer system 1900 also includes a memory 1904 coupled to bus 1910. The memory 1904, such as a random access memory (RAM) or other dynamic storage device, stores information including computer instructions. Dynamic memory allows information stored therein to be changed by the computer system 1900. RAM allows a unit of information stored at a location called a memory address to be stored and retrieved independently of information at neighboring addresses. The memory 1904 is also used by the processor 1902 to store temporary values during execution of computer instructions. The computer system 1900 also includes a read only memory (ROM) 1906 or other static storage device coupled to the bus 1910 for storing static information, including instructions, that is not changed by the computer system 1900. Also coupled to bus 1910 is a non-volatile (persistent) storage device 1908, such as a magnetic disk or optical disk, for storing information, including instructions, that persists even when the computer system 1900 is turned off or otherwise loses power.

Information, including instructions, is provided to the bus 1910 for use by the processor from an external input device 1912, such as a keyboard containing alphanumeric keys operated by a human user, or a sensor. A sensor detects conditions in its vicinity and transforms those detections into signals compatible with the signals used to represent information in computer system 1900. Other external devices coupled to bus 1910, used primarily for interacting with humans, include a display device 1914, such as a cathode ray tube (CRT) or a liquid crystal display (LCD), for presenting images, and a pointing device 1916, such as a mouse or a trackball or cursor direction keys, for controlling a position of a small cursor image presented on the display 1914 and issuing commands associated with graphical elements presented on the display 1914.

In the illustrated embodiment, special purpose hardware, such as an application specific integrated circuit (IC) 1920, is coupled to bus 1910. The special purpose hardware is configured to perform operations not performed by processor 1902 quickly enough for special purposes. Examples of application specific ICs include graphics accelerator cards for generating images for display 1914, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1900 also includes one or more instances of a communications interface 1970 coupled to bus 1910. Communication interface 1970 provides a two-way communication coupling to a variety of external devices that operate with their own processors, such as printers, scanners and external disks. In general the coupling is with a network link 1978 that is connected to a local network 1980 to which a variety of external devices with their own processors are connected. For example, communication interface 1970 may be a parallel port or a serial port or a universal serial bus (USB) port on a personal computer. In some embodiments, communications interface 1970 is an integrated services digital network (ISDN) card or a digital subscriber line (DSL) card or a telephone modem that provides an information communication connection to a corresponding type of telephone line. In some embodiments, a communication interface 1970 is a cable modem that converts signals on bus 1910 into signals for a communication connection over a coaxial cable or into optical signals for a communication connection over a fiber optic cable. As another example, communications interface 1970 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables.

Signals include man-made variations in amplitude, frequency, phase, polarization or other physical properties of carrier waves. For wireless links, the communications interface 1970 sends and receives electrical, acoustic or electromagnetic signals, including infrared and optical signals, that carry information streams, such as digital data.

The term computer-readable medium is used herein to refer to any medium that participates in providing information to processor 1902, including instructions for execution. Such a medium may take many forms, including, but not limited to, non-volatile media, volatile media and transmission media. Non-volatile media include, for example, optical or magnetic disks, such as storage device 1908. Volatile media include, for example, dynamic memory 1904. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1902, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1902, except for carrier waves and other signals.

Logic encoded in one or more tangible media includes one or both of processor instructions on a computer-readable storage media and special purpose hardware, such as ASIC 1920.

Network link 1978 typically provides information communication through one or more networks to other devices that use or process the information. For example, network link 1978 may provide a connection through local network 1980 to a host computer 1982 or to equipment 1984 operated by an Internet Service Provider (ISP). ISP equipment 1984 in turn provides data communication services through the public, world-wide packet-switching communication network of networks now commonly referred to as the Internet 1990. A computer called a server 1992 connected to the Internet provides a service in response to information received over the Internet. For example, server 1992 provides information representing video data for presentation at display 1914.

The invention is related to the use of computer system 1900 for implementing the techniques described herein. According to one embodiment of the invention, those techniques are performed by computer system 1900 in response to processor 1902 executing one or more sequences of one or more instructions contained in memory 1904. Such instructions, also called software and program code, may be read into memory 1904 from another computer-readable medium such as storage device 1908. Execution of the sequences of instructions contained in memory 1904 causes processor 1902 to perform the method steps described herein. In alternative embodiments, hardware, such as application specific integrated circuit 1920, may be used in place of or in combination with software to implement the invention. Thus, embodiments of the invention are not limited to any specific combination of hardware and software.

The signals transmitted over network link 1978 and other networks through communications interface 1970, carry information to and from computer system 1900. Computer system 1900 can send and receive information, including program code, through the networks 1980, 1990 among others, through network link 1978 and communications interface 1970. In an example using the Internet 1990, a server 1992 transmits program code for a particular application, requested by a message sent from computer 1900, through Internet 1990, ISP equipment 1984, local network 1980 and communications interface 1970. The received code may be executed by processor 1902 as it is received, or may be stored in storage device 1908 or other non-volatile storage for later execution, or both. In this manner, computer system 1900 may obtain application program code in the form of a signal on a carrier wave.

Various forms of computer readable media may be involved in carrying one or more sequence of instructions or data or both to processor 1902 for execution. For example, instructions and data may initially be carried on a magnetic disk of a remote computer such as host 1982. The remote computer loads the instructions and data into its dynamic memory and sends the instructions and data over a telephone line using a modem. A modem local to the computer system 1900 receives the instructions and data on a telephone line and uses an infra-red transmitter to convert the instructions and data to a signal on an infra-red a carrier wave serving as the network link 1978. An infrared detector serving as communications interface 1970 receives the instructions and data carried in the infrared signal and places information representing the instructions and data onto bus 1910. Bus 1910 carries the information to memory 1904 from which processor 1902 retrieves and executes the instructions using some of the data sent with the instructions. The instructions and data received in memory 1904 may optionally be stored on storage device 1908, either before or after execution by the processor 1902.

FIG. 20 illustrates a chip set 2000 upon which an embodiment of the invention may be implemented. Chip set 2000 is programmed to perform one or more steps of a method described herein and includes, for instance, the processor and memory components described with respect to FIG. 19 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 2000, or a portion thereof, constitutes a means for performing one or more steps of a method described herein.

In one embodiment, the chip set 2000 includes a communication mechanism such as a bus 2001 for passing information among the components of the chip set 2000. A processor 2003 has connectivity to the bus 2001 to execute instructions and process information stored in, for example, a memory 2005. The processor 2003 may include one or more processing cores with each core configured to perform independently. A multi-core processor enables multiprocessing within a single physical package. Examples of a multi-core processor include two, four, eight, or greater numbers of processing cores. Alternatively, or in addition, the processor 2003 may include one or more microprocessors configured in tandem via the bus 2001 to enable independent execution of instructions, pipelining, and multithreading. The processor 2003 may also be accompanied with one or more specialized components to perform certain processing functions and tasks such as one or more digital signal processors (DSP) 2007, or one or more application-specific integrated circuits (ASIC) 2009. A DSP 2007 typically is configured to process real-world signals (e.g., sound) in real time independently of the processor 2003. Similarly, an ASIC 2009 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 2003 and accompanying components have connectivity to the memory 2005 via the bus 2001. The memory 2005 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 2005 also stores the data associated with or generated by the execution of one or more steps of the methods described herein.

FIG. 21 is a diagram of exemplary components of a mobile terminal 2100 (e.g., cell phone handset) for communications, which is capable of operating in the system of FIG. 1A, according to one embodiment. In some embodiments, mobile terminal 2101, or a portion thereof, constitutes a means for performing one or more steps described herein. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 2103, a Digital Signal Processor (DSP) 2105, and a receiver/transmitter unit including a microphone gain control unit and a speaker gain control unit. A main display unit 2107 provides a display to the user in support of various applications and mobile terminal functions that perform or support the steps as described herein. The display 2107 includes display circuitry configured to display at least a portion of a user interface of the mobile terminal (e.g., mobile telephone). Additionally, the display 2107 and display circuitry are configured to facilitate user control of at least some functions of the mobile terminal. An audio function circuitry 2109 includes a microphone 2111 and microphone amplifier that amplifies the speech signal output from the microphone 2111. The amplified speech signal output from the microphone 2111 is fed to a coder/decoder (CODEC) 2113.

A radio section 2115 amplifies power and converts frequency in order to communicate with a base station, which is included in a mobile communication system, via antenna 2117. The power amplifier (PA) 2119 and the transmitter/modulation circuitry are operationally responsive to the MCU 2103, with an output from the PA 2119 coupled to the duplexer 2121 or circulator or antenna switch, as known in the art. The PA 2119 also couples to a battery interface and power control unit 2120.

In use, a user of mobile terminal 2101 speaks into the microphone 2111 and his or her voice along with any detected background noise is converted into an analog voltage. The analog voltage is then converted into a digital signal through the Analog to Digital Converter (ADC) 2123. The control unit 2103 routes the digital signal into the DSP 2105 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 2125 for compensation of any frequency-dependent impairments that occur during transmission though the air such as phase and amplitude distortion. After equalizing the bit stream, the modulator 2127 combines the signal with a RF signal generated in the RF interface 2129. The modulator 2127 generates a sine wave by way of frequency or phase modulation. In order to prepare the signal for transmission, an up-converter 2131 combines the sine wave output from the modulator 2127 with another sine wave generated by a synthesizer 2133 to achieve the desired frequency of transmission. The signal is then sent through a PA 2119 to increase the signal to an appropriate power level. In practical systems, the PA 2119 acts as a variable gain amplifier whose gain is controlled by the DSP 2105 from information received from a network base station. The signal is then filtered within the duplexer 2121 and optionally sent to an antenna coupler 2135 to match impedances to provide maximum power transfer. Finally, the signal is transmitted via antenna 2117 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 2101 are received via antenna 2117 and immediately amplified by a low noise amplifier (LNA) 2137. A down-converter 2139 lowers the carrier frequency while the demodulator 2141 strips away the RF leaving only a digital bit stream. The signal then goes through the equalizer 2125 and is processed by the DSP 2105. A Digital to Analog Converter (DAC) 2143 converts the signal and the resulting output is transmitted to the user through the speaker 2145, all under control of a Main Control Unit (MCU) 2103 which can be implemented as a Central Processing Unit (CPU) (not shown).

The MCU 2103 receives various signals including input signals from the keyboard 2147. The keyboard 2147 and/or the MCU 2103 in combination with other user input components (e.g., the microphone 2111) comprise a user interface circuitry for managing user input. The MCU 2103 runs a user interface software to facilitate user control of at least some functions of the mobile terminal 2101 as described herein. The MCU 2103 also delivers a display command and a switch command to the display 2107 and to the speech output switching controller, respectively. Further, the MCU 2103 exchanges information with the DSP 2105 and can access an optionally incorporated SIM card 2149 and a memory 2151. In addition, the MCU 2103 executes various control functions required of the terminal. The DSP 2105 may, depending upon the implementation, perform any of a variety of conventional digital processing functions on the voice signals. Additionally, DSP 2105 determines the background noise level of the local environment from the signals detected by microphone 2111 and sets the gain of microphone 2111 to a level selected to compensate for the natural tendency of the user of the mobile terminal 2101.

The CODEC 2113 includes the ADC 2123 and DAC 2143. The memory 2151 stores various data including call incoming tone data and is capable of storing other data including music data received via, e.g., the global Internet. The software module could reside in RAM memory, flash memory, registers, or any other form of writable storage medium known in the art. The memory device 2151 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 2149 carries, for instance, important information, such as the cellular phone number, the carrier supplying service, subscription details, and security information. The SIM card 2149 serves primarily to identify the mobile terminal 2101 on a radio network. The card 2149 also contains a memory for storing a personal telephone number registry, text messages, and user specific mobile terminal settings.

In some embodiments, the mobile terminal 2101 includes a digital camera comprising an array of optical detectors, such as charge coupled device (CCD) array 2165. The output of the array is image data that is transferred to the MCU for further processing or storage in the memory 2151 or both. In the illustrated embodiment, the light impinges on the optical array through a lens 2163, such as a pin-hole lens or a material lens made of an optical grade glass or plastic material. In the illustrated embodiment, the mobile terminal 2101 includes a light source 2161, such as a LED to illuminate a subject for capture by the optical array, e.g., CCD 2165. The light source is powered by the battery interface and power control module 2120 and controlled by the MCU 2103 based on instructions stored or loaded into the MCU 2103.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

4. REFERENCES

Each of the references are incorporated by reference herein with the exception of language not consistent with the terminology used herein.

1 Walsh, D. I., Kong, D. S., Murthy, S. K. & Carr, P. A. Enabling Microfluidics: from Clean Rooms to Makerspaces. Trends in Biotechnology (2017).
2 Nam, K.-H., Smith, A. S., Lone, S., Kwon, S. & Kim, D.-H. Biomimetic 3D tissue models for advanced high-throughput drug screening. Journal of laboratory automation 20, 201-215 (2015).
3 Konar, D., Devarasetty, M., Yildiz, D. V., Atala, A. & Murphy, S. V. Lung-On-A-Chip Technologies for Disease Modeling and Drug Development. Biomedical engineering and computational biology 7, 17 (2016).
4 Rezaei Kolahchi, A. et al. Microfluidic-Based Multi-Organ Platforms for Drug Discovery. Micromachines 7, 162 (2016).
5 Spira, M. E. & Hai, A. Multi-electrode array technologies for neuroscience and cardiology. Nature nanotechnology 8, 83-94 (2013).
6 Kim, J.-H., Kang, G., Nam, Y. & Choi, Y.-K. Surface-modified microelectrode array with flake nanostructure for neural recording and stimulation. Nanotechnology 21, 085303 (2010).
7 Larraneta, E., Lutton, R. E., Woolfson, A. D. & Donnelly, R. F. Microneedle arrays as transdermal and intradermal drug delivery systems: Materials science, manufacture and commercial development. Materials Science and Engineering: R: Reports 104, 1-32 (2016).
8 Temiz, Y., Lovchik, R. D., Kaigala, G. V. & Delamarche, E. Lab-on-a-chip devices: How to close and plug the lab? Microelectronic Engineering 132, 156-175 (2015).
9 Wainger, B. J., E. Kiskinis, C. Mellin, O. Wiskow, S. S. W. Han, J. Sandoe, N. P. Perez, L. A. Williams, S. Lee, G. Boulting, J. D. Berry, R. H. Brown, M. E. Cudkowicz, B. P. Bean, K. Eggan and C. J. Woolf. "Intrinsic Membrane Hyperexcitability of Amyotrophic Lateral Sclerosis Patient-Derived Motor Neurons." Cell Reports 7, no. 1 (2014): 1-11.
10 Woodard, C. M., B. A. Campos, S. H. Kuo, M. J. Nirenberg, M. W. Nestor, M. Zimmer, E. V. Mosharov, D. Sulzer, H. Y. Zhou, D. Paull, L. Clark, E. E. Schadt, S. P. Sardi, L. Rubin, K. Eggan, M. Brock, S. Lipnick, M. Rao, S. Chang, A. Q. Li and S. A. Noggle. "Ipsc-Derived Dopamine Neurons Reveal Differences between Monozygotic Twins Discordant for Parkinson's Disease." Cell Reports 9, no. 4 (2014): 1173-1182.
11 Ghane-Motlagh, B. & Sawan, M. in Advances in Biomedical Engineering (ICABME), 2013 2nd International Conference on. 38-41 (IEEE).

12 Kim, R., Joo, S., Jung, H., Hong, N. & Nam, Y. Recent trends in microelectrode array technology for in vitro neural interface platform. Biomedical Engineering Letters 4, 129-141 (2014).
13 Ita, K. Transdermal delivery of drugs with microneedles—Potential and challenges. Pharmaceutics 7, 90-105 (2015).
14 Chen, W., Li, H., Shi, D., Liu, Z. & Yuan, W. Microneedles as a delivery system for gene therapy. Frontiers in pharmacology 7 (2016).
15 Runyan, W. R. & Bean, K. E. Semiconductor integrated circuit processing technology. (Addison Wesley Publishing Company, 1990).
16 O'Mahony, C. Structural characterization and in-vivo reliability evaluation of silicon microneedles. Biomedical microdevices 16, 333-343 (2014).
17 Wang, P. M., Cornwell, M., Hill, J. & Prausnitz, M. R. Precise microinjection into skin using hollow microneedles. Journal of investigative dermatology 126, 1080-1087 (2006).
18 Donnelly, R. F., Singh, T. R. R. & Woolfson, A. D. Microneedle-based drug delivery systems: microfabrication, drug delivery, and safety. Drug delivery 17, 187-207 (2010).
19 Indermun, S. et al. Current advances in the fabrication of microneedles for transdermal delivery. Journal of controlled release 185, 130-138 (2014).
20 Choi, S.-O. et al. An electrically active microneedle array for electroporation. Biomedical microdevices 12, 263-273 (2010).
21 Aoyagi, S., Izumi, H., Isono, Y., Fukuda, M. & Ogawa, H. Laser fabrication of high aspect ratio thin holes on biodegradable polymer and its application to a microneedle. Sensors and Actuators A: Physical 139, 293-302 (2007).
22 McAllister, D. V. et al. Microfabricated needles for transdermal delivery of macromolecules and nanoparticles: fabrication methods and transport studies. Proceedings of the National Academy of Sciences 100, 13755-13760 (2003).
23 Park, J.-H., Allen, M. G. & Prausnitz, M. R. Polymer microneedles for controlled-release drug delivery. Pharmaceutical research 23, 1008-1019 (2006).
24 Han, M. et al. A novel fabrication process for out-of-plane microneedle sheets of biocompatible polymer. Journal of Micromechanics and Microengineering 17, 1184 (2007).
25 Lippmann, J. M., Geiger, E. J. & Pisano, A. P. Polymer investment molding: method for fabricating hollow, microscale parts. Sensors and Actuators A: Physical 134, 2-10 (2007).
26 Sullivan, S. P., Murthy, N. & Prausnitz, M. R. Minimally invasive protein delivery with rapidly dissolving polymer microneedles. Advanced materials 20, 933-938 (2008).
27 Chu, L. Y., Choi, S. O. & Prausnitz, M. R. Fabrication of dissolving polymer microneedles for controlled drug encapsulation and delivery: bubble and pedestal microneedle designs. Journal of pharmaceutical sciences 99, 4228-4238 (2010).
28 Kim, Y.-C., Quan, F.-S., Compans, R. W., Kang, S.-M. & Prausnitz, M. R. Formulation of microneedles coated with influenza virus-like particle vaccine. Aaps Pharmscitech 11, 1193-1201 (2010).
29 Donnelly, R. F. et al. Design, optimization and characterisation of polymeric microneedle arrays prepared by a novel laser-based micromoulding technique. Pharmaceutical research 28, 41-57 (2011).
30 Donnelly, R. F. et al. Hydrogel-forming microneedles prepared from "super swelling" polymers combined with lyophilised wafers for transdermal drug delivery. PLoS One 9, e111547 (2014).
31 Huang, H. & Fu, C. Different fabrication methods of out-of-plane polymer hollow needle arrays and their variations. Journal of Micromechanics and Microengineering 17, 393 (2007).
32 Ito, Y., Hagiwara, E., Saeki, A., Sugioka, N. & Takada, K. Feasibility of microneedles for percutaneous absorption of insulin. European journal of pharmaceutical sciences 29, 82-88 (2006).
33 Glick, C. C. et al. Rapid assembly of multilayer microfluidic structures via 3D-printed transfer molding and bonding. Microsystems & Nanoengineering 2, 16063 (2016).
34 https://all3dp.com/l/best-resin-dlp-sla-3d-printer-kit-stereolithography/
35 Rajaraman, S. in 231st ECS Meeting (May 28-Jun. 1, 2017). (Ecs).
36 Karnati, G., Aguilar, R., Arrowood, C., Ross, J. & Rajaraman, S. Rajaraman. Micromachining on and of Transparent Polymers for Patterning Electrodes and Growing Electrically Active Cells for Biosensor Applications. Micromachines 8, 250 (2017).
37 https://www.axionbiosystems.com/
38 https://www.multichannelsystems.com/
39 https://www.support.formlabs.com/hc/en-us/articles/115000024604-post-curing-prints
40 https://www.adafruit.com/product/166
41 Gallagher, A., Ní Annaidh, A. & Bruyère, K. in IRCOBI Conference 2012, 12-14 Sep. 2012, Dublin (Ireland). (International Research Council on the Biomechanics of Injury).
42 Ripolin, A. et al. Successful application of large microneedle patches by human volunteers. International journal of pharmaceutics 521, 92-101 (2017).
43 Shipulya, N. D., Konakov, S. A. & Krzhizhanovskaya, V. V. Development and simulation of microfluidic Wheatstone bridge for high-precision sensor. Journal of Physics: Conference Series, 738, 1 (2016).

What is claimed is:
1. A microelectrode array (MEA) produced by a method comprising:
applying a coarse scale additive process, with an additive device and a first material, to form an object, wherein the coarse scale is a dimension not less than about 100 µm; and
applying a biocompatible fine scale subtractive process, with a subtractive device, to the object, wherein the fine scale is a dimension not greater than about 1000 µm;
wherein the applying the coarse scale additive process comprises;
3D printing a base of the object with a 3D printer using an optical signal oriented at an angle with respect to a surface of the first material, wherein a value of the angle is in a range from about 30 degrees to about 60 degrees, and wherein the coarse scale dimension is based on the value of the angle and
lamination of a biocompatible adhesive to define an insulation layer of the object; and
wherein the applying the biocompatible fine scale subtractive process comprises micromachining with the subtractive device to fabricate a plurality of microelectrode recording sites in the insulation layer.

2. The microelectrode array as recited in claim 1, wherein the method further comprises moving, with a moving device, the object between the additive device and the subtractive device.

3. The microelectrode array as recited in claim 1, wherein the MEA comprises at least one of a diameter in a range from about 1 µm to about 150 µm, an average 1 kHz impedance in a range from about 20 kΩ to about 200 kΩ and a double layer capacitance of less than about 10 µF.

4. The microelectrode array as recited in claim 1, wherein the MEA comprises a diameter in a range from about 1 µm to about 150 µm, an average 1 kHz impedance in a range from about 20 kΩ to about 200 kΩ and a double layer capacitance of less than about 10 µF.

5. The microelectrode array as recited in claim 1, wherein the first material is a resin, wherein the optical signal is an ultraviolet (UV) laser or UV light emitting diode (LED), and wherein the 3D printing is performed by focusing the UV laser or UV LED onto the resin using a scanner system, wherein the scanner system includes one or more mirrors and lenses that direct the UV laser or UV LED at an angle with respect to the surface of the resin.

6. The microelectrode array as recited in claim 5, wherein the resin is a photopolymer resin such that the resin is photochemically solidified and forms a single layer of the base of the object based on the UV laser or UV LED being directed at the resin.

7. The microelectrode array as recited in claim 6, wherein the base of the object comprises a plurality of layers wherein each respective layer is photochemically solidified resin formed based on the UV laser or UV LED being directed at photopolymer resin at the angle with respect to the surface of the resin.

8. The microelectrode array as recited in claim 1, wherein the insulation layer of the object is formed by:
    defining a shape of a Poly Ethylene Terephthalate (PET) biocompatible adhesive using a cutting device;
    removing a liner on the Poly Ethylene Terephthalate (PET) biocompatible adhesive;
    affixing the PET biocompatible adhesive to the object; and
    pressing the PET biocompatible adhesive and the object together using a laminating press.

9. The microelectrode array as recited in claim 1, wherein the insulation layer of the object is formed by biocompatible additive spin coating including:
    applying a photoresist including a biocompatible adhesive to the object;
    spin coating the object using a spin coater;
    heating the object using a heater; and
    exposing the object to ultra violet (UV) radiation using a UV lamp.

10. The microelectrode array as recited in claim 1, wherein the applying the biocompatible coarse scale additive process further comprises ink casting to define conductive traces on the object.

11. The microelectrode array as recited in claim 10, wherein the ink casting step comprises:
    coating the object with conductive ink using a cotton swab;
    curing the object using a heater;
    rinsing the object in isopropyl alcohol; and
    drying the object with a nitrogen gun.

12. The microelectrode array as recited in claim 1, wherein the subtractive device is a laser, wherein a plurality of recording sites in the insulation layer are formed by aligning the laser with the insulation layer of the object and operating the laser to fabricate the plurality of recording sites in the insulation layer using the subtractive process.

13. The microelectrode array produced by a method as recited in claim 12, wherein the laser is operated with at least one of a wavelength of about 532 nm, a spot size less than 100 µm×100 µm, a repetition rate of about 50 Hz and an energy level from about 25 mJ to about 50 mJ.

14. The microelectrode array as recited in claim 1, wherein the subtractive device is a drill bit and wherein the applying the biocompatible fine scale subtractive process further comprises micromilling with the drill bit to fabricate a plurality of microelectrode recording sites in the insulation layer.

15. The microelectrode array as recited in claim 14, wherein micromilling step includes fabricating the plurality of microelectrode recording sites using the drill bit, wherein the drill bit has a thickness in a range from about 200 µm to about 300 µm and wherein the drill bit is operated at a drilling speed of about 180 holes per minute.

16. The microelectrode array as recited in claim 1, wherein the applying the biocompatible coarse scale additive process further comprises depositing microelectrode material in the plurality of microelectrode recording sites based on:
    preparing a platinum solution including porous platinum;
    transferring the platinum solution to the plurality of microelectrode recording sites;
    waiting for a minimum time period for platinum coverage of the plurality of microelectrode recording sites.

17. The microelectrode array as recited in claim 1, wherein the 3D printing forms the base of the object with one or more non-planar surfaces.

18. A microelectrode array (MEA) produced by a method comprising:
    applying a biocompatible coarse scale additive process, with an additive device and a biocompatible material, to form an object, wherein the coarse scale is a dimension not less than about 100 µm;
    applying a biocompatible fine scale subtractive process, with a subtractive device, to the object, wherein the fine scale is a dimension not greater than about 1000 µm; and
    moving the object between the additive device and the subtractive device, the MEA comprising at least one of a diameter in a range from about 1 µm to about 150 µm, an average 1 kHz impedance in a range from about 20 kΩ to about 200 kΩ and a double layer capacitance of less than about 10 µF;
    wherein the applying the biocompatible coarse scale additive process comprises;
        3D printing a base of the object with a 3D printer using an optical signal oriented at an angle with respect to a surface of the biocompatible material, wherein a value of the angle is in a range from about 30 degrees to about 60 degrees and wherein the coarse scale dimension is based on the value of the angle, and
        spin coating or lamination of a biocompatible adhesive to define an insulation layer of the object; and
    wherein the applying the biocompatible fine scale subtractive process comprises micromachining with a laser to fabricate a plurality of microelectrode recording sites in the insulation layer.

* * * * *